United States Patent
Sall et al.

(10) Patent No.: US 6,620,837 B1
(45) Date of Patent: Sep. 16, 2003

(54) ANTITHROMBOTIC AGENTS

(75) Inventors: Daniel Jon Sall, Greenwood, IN (US); John Eldon Toth, Indianapolis, IN (US); Kumiko Takeuchi, Indianapolis, IN (US); Todd Johnathan Kohn, Fishers, IN (US); Jolie Anne Bastian, Beech Grove, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/111,508

(22) PCT Filed: Nov. 3, 2000

(86) PCT No.: PCT/US00/28876

§ 371 (c)(1),
(2), (4) Date: Apr. 23, 2002

(87) PCT Pub. No.: WO01/36414

PCT Pub. Date: May 25, 2001

Related U.S. Application Data

(60) Provisional application No. 60/166,575, filed on Nov. 19, 1999.

(51) Int. Cl.$^7$ .................. A61K 31/40; C07D 405/00
(52) U.S. Cl. .................. 514/422; 548/525; 548/517
(58) Field of Search .................. 514/422; 548/525, 548/517

(56) References Cited

U.S. PATENT DOCUMENTS 6,265,575 B1 * 7/2001 Thrasher et al. ............ 540/596
6,350,774 B1 * 2/2002 Bach et al. .................. 514/422

FOREIGN PATENT DOCUMENTS

WO          WO 98/48804        * 11/1998

* cited by examiner

*Primary Examiner*—Deborah C. Lambkin
(74) *Attorney, Agent, or Firm*—Thomas E. Jackson; Arvie J. Anderson

(57) ABSTRACT

This application relates to novel compounds of formula (I) (and their pharmaceutically acceptable salts), as defined herein, processes and intermediates for their preparation, pharmaceutical formulations comprising the novel compounds of formula (I), and the use of defined compounds of formula (I) as thrombin inhibitors.

16 Claims, No Drawings

ANTITHROMBOTIC AGENTS

This application is a 371 of PCT/US/00/28876 Nov. 3, 2000 which claims the benefit of U.S. Provisional Application No. 60/166,575, filed Nov. 19, 1999.

This invention relates to thrombin inhibitors which are useful anticoagulants in mammals. In particular it relates to substituted benzo[b]thiophene derivatives having high anticoagulant activity, and antithrombotic activity. Thus, this invention relates to new inhibitors of thrombin, pharmaceutical compositions containing the compounds as active ingredients, and the use of the compounds as anticoagulants for prophylaxis and treatment of pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the antithrombotic agents are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation.

Anticoagulation currently is achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Antithrombotic diamines are disclosed in International Patent Application Publication Number WO 97/25033, WO 98/48798 and WO 98/49161. Compounds of this invention have lower volumes of distribution and, therefore, improved pharmacokinetic properties over those of WO 97/25033, WO 98/48798 and WO 98/49161.

Although the heparins and coumarins are effective anticoagulants, no widely used drug has yet emerged from the promise for this class of compounds, there still exists a need for anticoagulants which act selectively on thrombin, and which, independent of antithrombin III, exert inhibitory action shortly after administration, preferably by an oral route, and do not interfere with lysis of blood clots, as required to maintain hemostasis.

According to the invention there is provided a compound of formula I (or a pharmaceutically acceptable salt thereof)

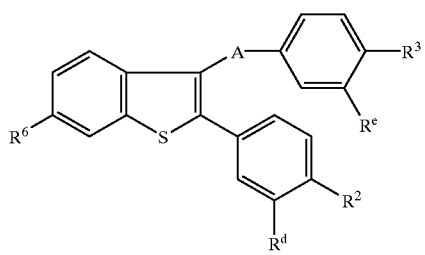

I wherein

A is carbonyl or methylene;

$R^d$ is —[O—$(CH_2)_d$]$_c$—$R^c$ in which c is 0 or 1; d is 1, 2, or 3; and $R^c$ is carboxy, [(1–4C)alkoxy]carbonyl, hydroxymethyl or carbamoyl; provided that if c is 0, $R^c$ is carboxy, [(1–4C)alkoxy]carbonyl or carbamoyl;

$R^e$ is hydrogen, methyl, methoxy or halo;

$R^2$ is $R^{2a}$ or $R^{2b}$ in which $R^{2a}$ is —$X^2$—$(CH_2)_n$—$R^f$ in which $X^2$ is a direct bond, methylene or O; n is 1, 2 or 3; and $R^f$ is 5-tetrazolyl, carboxy, [(1–4C)alkoxy]carbonyl or hydroxymethyl;

$R^{2b}$ is —$X^2$—$(CH_2)_m$—$NR^aR^b$ in which $X^2$ is a direct bond, methylene or O; m is 1, 2 or 3; provided that when m is 1, then $X^2$ is a direct bond; and $R^a$ and $R^b$ are independently hydrogen or (1–3C)alkyl or the group $NR^aR^b$ is pyrrolidino, piperidino or morpholino;

$R^3$ is $R^{3a}$ or $R^{3b}$ in which $R^{3a}$ is 2-(2-oxopyrolidin-1-yl)ethoxy;

provided that $R^2$ is $R^{2b}$ when $R^3$ is $R^{3a}$;

$R^{3b}$ is —$X^3$—$(CH_2)_s$—$NR^sR^t$ in which $X^3$ is a direct bond, methylene or O; s is 1 or 2; provided that when s is 1, then $X^3$ is a direct bond; and $R^s$ and $R^t$ are independently hydrogen or (1–3C)alkyl or the group $NR^sR^t$ is pyrrolidino, piperidino or morpholino; and $R^6$ is hydrogen, hydroxy or methoxy.

As a further aspect of the invention, there is provided a prodrug (or a pharmaceutically acceptable salt thereof) of any of the above described thrombin inhibiting compounds of formula I which will form a prodrug.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted.

It will be appreciated that certain compounds of formula I (or salts or prodrugs, etc.) may exist in, and be isolated in, isomeric forms, including cis- or trans-isomers, as well as optically active, racemic, or diastereomeric forms. It is to be understood that the present invention encompasses a compound of formula I as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against thrombin, it being well known in the art how to prepare or isolate particular forms and how to determine inhibitory properties against thrombin by standard tests including those described below.

In addition, a compound of formula I (or salt of prodrug, etc.) may exhibit polymorphism or may form a solvate with water or an organic solvent. The present invention also encompasses any such polymorphic form, any solvate or any mixture thereof.

Particular values are listed below for radicals, substituents, and ranges, for illustration only, and they do not exclude other defined values or other values within defined ranges for the radicals and substituents.

A particular value for a (1–3C)alkyl group is, for example, methyl, ethyl, propyl or isopropyl, and for a (1–4C)alkoxy group is, for example, methoxy, ethoxy, isopropoxy or t-butoxy.

A particular value, independently, for A is carbonyl or methylene;

for $R^d$ is carboxy, methoxycarbonyl, carbamoyl, 3-(ethoxycarbonyl)propoxy, 3-carboxypropoxy, 4-amino-4-oxobutoxy, 4-hydroxybutoxy, (t-butoxycarbonyl)methoxy, or carboxymethoxy;

for $R^e$ is hydrogen or methoxy;

for $R^2$ is 2-(1-pyrrolidinyl)ethoxy, 3-carboxypropoxy, or 3-(methoxycarbonyl)propoxy;

for $R^3$ is 2-(1-pyrrolidinyl)ethoxy, 1-pyrrolidinyl)methyl or 2-(2-oxopyrrolidin-1-yl)ethoxy; and for $R^6$ is hydrogen or hydroxy.

A particular value for $R^2$ is $R^{2a}$. A further particular value for $R^2$ is $R^{2b}$.

A particular value for $R^3$ is $R^{3a}$. A further particular value for $R^3$ is $R^{3b}$ and $R^2$ is $R^{2b}$.

A particular compound of formula I is one in which $R^d$ is methoxycarbonyl, $R^e$ is hydrogen and $R^3$ is 2-(2-oxopyrrolidin-1-yl)ethoxy.

A further particular compound of formula I is 2-[3-methoxycarbonyl-4-[2-(1-pyrrolidinyl)ethoxy]-phenyl]-3-[4-[2-(2-oxopyrrolidin-1-yl)ethoxy]benzyl]benzo[b]-thiophene.

Specific compounds of formula I are described in the accompanying Examples. The compound described as Example 13, 2-[3-carboxymethoxy-4-[2-(1-pyrrolidinyl)-ethoxy]phenyl]-3-[4-[2-(2-oxopyrrolidin-1-yl)ethoxy] benzyl]-benzo[b]thiophene, (or a pharmaceutically acceptable salt thereof) is a preferred species.

A pharmaceutically acceptable salt of an antithrombotic agent of the instant invention includes one which is an acid-addition salt made with an acid which provides a pharmaceutically acceptable anion. Thus, an acid addition salt of a novel compound of formula I as provided above made with an acid which affords a pharmaceutically acceptable anion or, for a compound which contains an acidic moiety, provides a particular aspect of the invention. Examples of such acids are provided hereinbelow.

As an additional aspect of the invention there is provided a pharmaceutical formulation comprising in association with a pharmaceutically acceptable carrier, diluent or excipient, a compound of formula I (or a pharmaceutically acceptable salt thereof) as provided in any of the above descriptions.

A compound of formula I may be made by processes which include processes known in the chemical art for the production of compounds structurally related to a compound of formula I or by a novel process described herein. A process for a compound of formula I (or a pharmaceutically acceptable salt thereof), novel processes for a compound of formula I and novel intermediates for the manufacture of a compound of formula I as defined above provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

Thus, there is provided a process for preparing a compound of formula I (or a pharmaceutically acceptable salt thereof) as provided in any of the above descriptions which is selected from:

(A) for a compound of formula I in which $R^c$ is [(1–4C) alkoxy]carbonyl, oxidatively esterifying a corresponding compound of formula I in which $R^c$ is formyl using an oxidizing agent and the corresponding (1–4C) alkanol. The oxidative esterification may be carried out by a conventional manner consistent with the structure of the compound of formula I, for example, using manganese (IV) oxide and sodium cyanide in dry methanol as described in Example 1-C;

(B) for a compound of formula I in which $R^c$ is carbamoyl, oxidatively amidating a corresponding compound of formula I in which $R^c$ is formyl using an oxidizing agent and ammonia. The oxidative amidation may be carried out by a conventional procedure consistent with the structure of the compound of formula I, for example, using sodium cyanide and manganese (IV) oxide in the presence of ammonia as described in Example 4;

(C) for a compound of formula I in which $R^c$ is carboxy, oxidizing the formyl group of a corresponding compound of formula I in which $R^c$ is formyl, for example by using a procedure such as that described in Example 5-J;

(D) for a compound of formula I in which $R^c$ is [(1–4C) alkoxy]carbonyl, esterifying the carboxy group of a corresponding compound of formula I in which $R^c$ is carboxy, for example by using a procedure such as that described in Example 1-C;

(E) for a compound of formula I in which $R^d$ is —O—$(CH_2)_d$—$R^c$, alkylating the hydroxy group of a corresponding compound of formula I in which $R^d$ is hydroxy using an alkylating agent of formula X—$(CH_2)_d$—$R^c$ (or a protected derivative thereof) where X is a conventional leaving group, using a standard alkylation procedure such as that described in Example 6-G;

(F) for a compound of formula I in which $R^c$ is carbamoyl, amidating the acid or an activated derivative thereof of a corresponding compound of formula I in which $R^c$ is carboxy. Conveniently, the addition is carried out using a lower alkyl ester, ammonium chloride and trimethyl aluminum in toluene, for example as described in Example 8;

(G) for a compound of formula I in which $R^c$ is hydroxymethyl, reducing the ester of a corresponding compound of formula I in which $R^c$ is [(1–4C)alkoxy] carbonyl, for example by using a procedure such as that described in Example 9;

whereafter, for any of the above procedures, when a functional group is protected using a protecting group, removing the protecting group;

whereafter, for any of the above procedures, when a pharmaceutically acceptable salt of a compound of formula I is required, it is obtained by reacting the basic form of such a compound of formula I with an acid affording a physiologically acceptable counterion, or, for a compound of formula I which bears an acidic moiety, reacting the acidic form of such a compound of formula I with a base which affords a pharmaceutically acceptable cation, or by any other conventional procedure;

and wherein, unless otherwise described, A, $R^d$, $R^e$, $R^2$, $R^3$ and $R^6$ have the values described above.

As used herein, a leaving group is a moiety which is displaced in a nucleophilic substitution reaction, for example a halo group (such as chloro, bromo or iodo), a sulfonate ester group (such as methylsulfonyloxy, p-toluylsulfonyloxy or trifluoromethylsulfonyloxy), or the reactive species derived from treating an alcohol with triphenylphospine, diethyl azodicarboxylate and triethyl amine (in a Mitsunobu reaction).

As mentioned above, a compound corresponding to a compound of formula I but in which a functional group is protected may serve as an intermediate for a compound of formula I. Accordingly, such protected intermediates for a novel compound of formula I provide further aspects of the invention. Thus, as one particular aspect of the invention, there is provided a compound corresponding to a novel compound of formula I as defined above in which $R^6$ which is hydroxy, but in which the corresponding substituent is —$OR^p$ in place of hydroxy, wherein $R^p$ is a phenol protecting group other than methyl. Phenol protecting groups are well known in the art, for example as described in T. W. Greene and P. G. M. Wuts, "Protecting Groups in Organic Synthesis" (1991). Particular values of $R^p$ include, for example, isopropyl. Further, $R^p$ may denote a functionalized resin, for example as disclosed in H. V. Meyers, et al., *Molecular Diversity*, (1995), 1, 13–20.

As mentioned above, the invention includes pharmaceutically acceptable salts of the thrombin inhibiting compounds defined by the above formula I. A compound of formula I which bears an acidic moiety forms salts with pharmaceutically acceptable bases. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as triethylamine, morpholine, piperidine and triethanolamine. The potassium and sodium salt forms are particularly preferred.

A particular compound of formula I which possesses one or more sufficiently basic functional groups to react with any of a number of inorganic and organic acids affording a physiologically acceptable counterion forms a pharmaceutically acceptable acid addition salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

If not commercially available, the necessary starting materials for the preparation of a compound of formula I may be prepared by procedures which are selected from standard techniques of organic chemistry, including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. Starting materials which are novel provide another aspect of the invention.

Starting material phenolic compounds of formula I where $R^2$ is hydroxy may be prepared and used by methods similar to those described in Example 1, parts E through I.

Starting material for diesteric compounds of formula I where $R^2$ and $R^d$ and [(1–4C)alkoxy]carbonyl may be prepared by methods similar to those described in WO 98/48798, Example 19-B.

Starting material acidic compounds of procedures similar to those described in WO 97/25033, Example 1, part A and Graham, S. C., et al. *J. Med. Chem.*, 1989, 32, 2548–2554.

A starting material ether, such as 4-bromo-2-methoxyphenyl 2-(1-pyrrolidinyl)ethyl ether, may be prepared by procedures similar to those in Example 6, Part A.

Starting material for a compound of formula I where $R^2$ is $R^{2b}$ and $R^3$ is $R^{3a}$ may be prepared by procedures similar to those described in WO 98/48798, Example 18, Part A.

Generally, the compounds of the invention are isolated best in the form of acid addition salts. Salts of the compounds of formula I formed with acids such as those mentioned above are useful as pharmaceutically acceptable salts for administration of the antithrombotic agents and for preparation of formulations of these agents. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley & Sons, 1981.

The compounds of the invention are believed to selectively inhibit thrombin over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

Many of the antithrombotic compounds disclosed in the prior art are lipophilic and, therefore, undergo high volumes of distribution from the plasma component and into the tissues. Since thrombin resides in the plasma, this tissue distribution is not preferred. The compounds of the present invention possess hydrophilic substituents in an effort to reduce overall lipophilicity of the molecules, thereby decreasing the distribution and increasing their plasma concentrations. Data in Table 1 below confirms that the compounds of the present invention have lower volumes of distribution and, therefore, better pharmacokinetic properties than their corresponding compounds of formula I in which $R^d$ is hydrogen.

The Volume of Distribution ($V_D$) was calculated according to the standard equation:

$$V_D = \text{Clearance}/K$$

where Clearance=Dose (ug)/AUC (ug/ml) where AUC is the amount of drug present in plasma following oral dosing and is measured as the area under a curve of drug concentration versus time. $K(h^{-1})$ is the elimination rate constant.

TABLE 1

Comparison of Volumes of Distribution ($V_D$)

| Ex.# | $R^d$ Value | $V_D$ (L/kg) | Comparator In which $R^d$ = H $V_D$ (L/kg) | Reference |
|---|---|---|---|---|
| 1 | carboxy | 1.27 | 29.0 | (a) |
| 2 | carboxy | 0.46 | 1.3 | (b) |
| 4 | carbamoyl | 3.36 | N/D | (c) |
| 8 | 3-(carbomoyl)butoxy | 13.53 | 26.6 | (d) |
| 11 | 3-(carboxy)butoxy | 5.13 | 6.4 | (e) |
| 13 | carboxymethoxy | N/D | 26.6 | (f) |

(a) WO 97/25033, Example 3
(b) Available via Saponification of Example 13
(c) WO 98/48798, Example 8
(d) WO 98/49161, Example 20
(e) WO 98/49161, Example 19
(f) WO 98/49161, Example 20
N/D = Not Determined The invention provides a method of inhibiting thrombin in mammalian blood comprising using an effective amount of a compound of formula I (or a pharmaceutically acceptable salt thereof) as provided in any of the descriptions herein.

The invention in one of its aspects provides a method of inhibiting thrombin in a mammal comprising administering to a mammal in need of treatment an effective (thrombin inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in mammals comprising administering to a mammal in need of treatment an effective (coagulation inhibiting) dose of a compound of formula I.

The thrombin inhibition, coagulation inhibition and thromboembolic disorder treatment contemplated by the present method includes both medical therapeutic and/or prophylactic treatment as appropriate.

In a further embodiment the invention relates to treatment, in a human or animal, of conditions where inhibition of thrombin is required. The compounds of the invention are expected to be useful in animals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally, parenterally e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides pharmaceutical formulations for use in the above described therapeutic method. Pharmaceutical formulations of the invention comprise an effective thrombin inhibiting amount of a compound of formula I in association with a pharmaceutically acceptable carrier, excipient or diluent. For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9 percent), 5 percent dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration. Another embodiment of the present invention is a pharmaceutical formulation comprising an effective amount of a novel compound of formula I or a pharmaceutically acceptable salt or solvate thereof in association with a pharmaceutically acceptable carrier, diluent or excipient therefor.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to Formula I or a pharmaceutically acceptable salt or solvate thereof.

Formulation 1: Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2: A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3: An aerosol solution is prepared containing the following components:

|  | Weight |
| --- | --- |
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10 % solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5: Capsules, each containing 80 mg of active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6: Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7: Suspensions, each containing 50 mg of active ingredient per 5 ml dose, are made as follows:

| Active ingredient | 50 mg |
|---|---|
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8: An intravenous formulation may be prepared as follows:

| Active ingredient | 100 mg |
|---|---|
| Isotonic saline | 1,000 mL |

The solution of the above ingredients generally is administered intravenously to a subject at a rate of 1 mL per minute.

The ability of the compounds of the present invention to be an effective and orally active thrombin inhibitor are evaluated in one or more of the following assays.

The compounds provided by the invention (formula I) selectively inhibit the action of thrombin in mammals. The inhibition of thrombin is demonstrated by in vitro inhibition of the amidase activity of thrombin as measured in an assay in which thrombin hydrolyzes the chromogenic substrate, N-benzoyl-L-phenylalanyl-L-valyl-L-arginyl-p-nitroanilide, N-benzoyl-L-Phe-L-Val-L-Arg-p-nitroanilide.

The assay is carried out by mixing 50 $\mu$L buffer (0.03 M Tris, 0.15 M NaCl, pH 7.4) with 25 $\mu$L of human thrombin solution (purified human thrombin, Enzyme Research Laboratories, South Bend, Ind., at 8 NIH units/mL) and 25 $\mu$L of test compound in a solvent (50% aqueous methanol (v:v)). Then 150 $\mu$L of an aqueous solution of the chromogenic substrate (at 0.25 mg/mL) are added and the rates of hydrolysis of the substrate are measured by monitoring the reactions at 405 nm for the release of p-nitroaniline. Standard curves are constructed by plotting free thrombin concentration against hydrolysis rate. The hydrolysis rates observed with test compounds are then converted to "free thrombin" values in the respective assays by use of the standard curves. The bound thrombin (bound to test compound) is calculated by subtracting the amount of free thrombin observed in each assay from the known initial amount of thrombin used in the assay. The amount of free inhibitor in each assay is calculated by subtracting the number of moles of bound thrombin from the number of moles of added inhibitor (test compound).

The Kass value is the hypothetical equilibrium constant for the reaction between thrombin and the test compound (I).

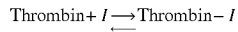

$$Kass = \frac{[Thrombin - I]}{[(Thrombin) \times (I)]}$$

Kass is calculated for a range of concentrations of test compounds and the mean value reported in units of liter per mole. In general, a thrombin inhibiting compound of formula I of the instant invention exhibits a Kass of $0.1 \times 10^6$ L/mole or much greater.

By substantially following the procedures described above for human thrombin, and using other human blood coagulation system serine proteases and using fibrinolytic system serine proteases, with the appropriate chromogenic substrates, identified below, the selectivity of the compounds of the present invention with respect to the coagulation factor serine proteases and to the fibronolytic serine proteases are evaluated as well as their substantial lack of interference with human plasma clot fibrinolysis.

Human factors X, Xa, IXa, XIa, and XIIa are purchased from Enzyme Research Laboratories, South Bend, Ind.; human urokinase from Leo Pharmaceuticals, Denmark; and recombinant activated Protein C (aPC) is prepared at Eli Lilly and Co. substantially according to U.S. Pat. No. 4,981,952. Chromogenic substrates: N-Benzoyl-Ile-Glu-Gly-Arg-p-nitroanilide (for factor Xa); N-Cbz-D-Arg-Gly-Arg-p-nitroanilide (for factor IXa assay as the factor Xa substrate); Pyroglutamyl-Pro-Arg-p-nitroanilide (for Factor XIa and for aPC); H-D-Pro-Phe-Arg-p-nitroanilide (for factor XIIa); and Pyroglutamyl-Gly-Arg-p-nitroanilide (for urokinase); are purchased from Kabi Vitrum, Stockholm, Sweden, or from Midwest Biotech, Fishers, Ind. Bovine trypsin is purchased from Worthington Biochemicals, Freehold, N.J., and human plasma kallikrein from Kabi Vitrum, Stockholm, Sweden. Chromogenic substrate H-D-Pro-Phe-Arg-p-nitroanilide for plasma kallikrein is purchased from Kabi Vitrum, Stockholm, Sweden. N-Benzoyl-Phe-Val-Arg-p-nitroanilide, the substrate for human thrombin and for trypsin, is synthesized according to procedures described above for the compounds of the present invention, using known methods of peptide coupling from commercially available reactants, or purchased from Midwest Biotech, Fishers, Ind.

Human plasmin is purchased from Boehringer Mannheim, Indianapolis, Ind.; nt-PA is purchased as single chain activity reference from American Diagnostica, Greenwich, Conn.; modified-t-PA6 (mt-PA6) is prepared at Eli Lilly and Company by procedure known in the art (See, Burck, et al., *J. Biol. Chem.*, 265, 5120–5177 (1990). Plasmin chromogenic substrate H-D-Val-Leu-Lys-p-nitroanilide and tissue plasminogen activator (t-PA) substrate H-D-Ile-Pro-Arg-p-nitroanilide are purchased from Kabi Vitrum, Stockholm, Sweden.

In the chromogenic substrates described above the three-letter symbols Ile, Glu, Gly, Pro, Arg, Phe, Val, Leu and Lys are used to indicate the corresponding amino acid group isoleucine, glutamic acid, glycine, proline, arginine, phenylalanine, valine, leucine and lysine, respectively.

Thrombin inhibitors preferably should spare fibrinolysis induced by urokinase, tissue plasminogen activator (t-PA) and steptokinase. This would be important to the therapeutic use of such agents as an adjunct to streptokinase, t-PA or urokinase thrombolytic therapy and to the use of such agents as an endogenous fibrinolysis-sparing (with respect to t-PA and urokinase) antithrombotic agents. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction I-2 according to previous procedures and specifications. Smith, *Biochem. J.*, 185, 1–11 (1980); and Smith, et al., *Biochemistry*, 11, 2958–2967, (1972). Human fibrinogen (98 percent pure/plasmin free) is from American Diagnostica, Greenwich, Conn. Radiolabeling of fibrinogen I-2 preparations is performed as previously reported. Smith, et al., *Biochemistry*, 11, 2958–2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 $\mu$L thrombin (73 NIH unit/mL) to 100 $\mu$L human plasma which contains 0.0229 $\mu$Ci 125-iodine labeled fibrinogen. Clot lysis is studied by overlaying the clots with 50 $\mu$L of urokinase or streptokinase (50, 100, or 1000 unit/mL) and incubating for 20 hours at room temperature. After incubation the tubes are centrifuged in a Beckman Microfuge. 25 $\mu$L of supernate is added into 1.0 mL volume of 0.03 M tris/0.15 M NaCl buffer for gamma counting. Counting controls 100 percent lysis are obtained by omitting thrombin (and substituting buffer). The thrombin inhibitors are evaluated for possible interference with fibrinolysis by including the compounds in the overlay solutions at 1, 5, and 10 $\mu$g/mL concentrations. Rough approximations of $IC_{50}$ values are estimated by linear extrapolations from data points to a value which would represent 50 percent of lysis for that particular concentration of fibrinolytic agent.

Anticoagulant Activity

Materials

Dog plasma and rat plasma are obtained from conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents Actin, Thromboplastin, Innovin and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M). The thrombin time (TT) is measured by adding 0.05 mL saline and 0.05 mL thrombin (10 NIH units/mL) to 0.05 mL test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous Shunt Model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29, 1982). In this model preferred compounds of the instant invention reduce the net clot weight to approximately 25–30% of control, or even lower, at an i.v. dose of 33.176 $\mu$mol/kg/h.

$FeCl_3$ Model of Arterial Injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20 percent) is expressed in terms of the actual weight of $FeCl_3$ only. To injure the artery and induce thrombosis, 2.85 $\mu$L is pipetted into the cuff to bathe the artery above the thermocouple probe. Arterial occlusion is indicated by a rapid drop in temperature. The time to occlusion is reported in minutes and represents the elapsed time between application of FeCl$_3$ and the rapid drop in vessel temperature (see K. D. Kurz, *Thromb. Res.*, 60:269, 1990).

Spontaneous Thrombolysis Model

In vitro data suggests that thrombin inhibitors inhibit thrombin and, at higher concentrations, may inhibit other serine proteases, such as plasmin and tissue plasminogen activator. To assess if the compounds inhibit fibrinolysis in vivo, the rate of spontaneous thrombolysis is determined by implanting a labeled whole blood clot into the pulmonary circulation. Rat blood (1 mL) is mixed rapidly with bovine thrombin (4 IU, Parke Davis) and $^{125}$I human Fibrogen (5 µCi, ICN), immediately drawn into silastic tubing and incubated at 37° C. for 1 hour. The aged thrombus is expelled from the tubing, cut into 1 cm segments, washed 3× in normal saline and each segment is counted in a gamma counter. A segment with known counts is aspirated into a catheter that is subsequently implanted into the jugular vein. The catheter tip is advanced to the vicinity of the right atrium and the clot is expelled to float into the pulmonary circulation. One hour after implant, the heart and lungs are harvested and counted separately. Thrombolysis is expressed as a percentage where:

$$\% \text{ Thrombolysis} = \frac{(\text{injected cpm} - \text{lung cpm})}{\text{injected cpm}} \times 100$$

The fibrinolytic dissolution of the implanted clot occurs time-dependently (see J. P. Clozel, *Cardiovas. Pharmacol.*, 12:520, 1988).

Coagulation Parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed with saline (0.1 mL) and bovine thrombin (0.1 mL, 30 U/mL in TRIS buffer; Parke Davis) at 37° C. For APTT, plasma (0.1 mL) and APTT solution (0.1 mL, Organon Teknika) are incubated for 5 minutes (37° C.) and CaCl$_2$ (0.1 mL, 0.025 M) is added to start coagulation. Assays are done in duplicate and averaged.

Index of Bioavailability

For a measure of bioactivity, plasma thrombin time (TT) serves as a substitute for the assay of parent compound on the assumption that observed increments in TT resulted from thrombin inhibition by parent only. The time course of the effect of the thrombin inhibitor upon TT is determined after i.v bolus administration to anesthetized rats and after oral treatment of fasted conscious rats. Due to limitations of blood volume and the number of points required to determine the time course from time of treatment to the time when the response returns to pretreatment values, two populations of rats are used. Each sample population represents alternating sequential time points. The average TT over the time course is used to calculate area under the curve (AUC). The index of bioavailability is calculated by the formula shown below and is expressed as percent relative activity.

The area under the curve (AUC) of the plasma TT time course is determined and adjusted for the dose. This index of bioavailability is termed "% Relative Activity" and is calculated as $$\% \text{ Relative Activity} = \frac{\text{AUC po}}{\text{AUC iv}} \times \frac{\text{Dose iv}}{\text{Dose po}} \times 100$$

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the FeCl$_3$ model of arterial injury and in the spontaneous thrombolysis model. Bolus injection volume is 1 mL/kg for i.v., and 5 mL/kg for p.o., and infusion volume is 3 mL/hr.

Statistics

Results are expressed as means +/− SEM. One-way analysis of variance is used to detect statistically significant differences and then Dunnett's test is applied to determine which means are different. Significance level for rejection of the null hypothesis of equal means is P<0.05.

Animals

Male dogs (Beagles; 18 months–2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66–74° F.; 45–50 percent relative humidity; and lighted from 0600–1800 hours.

Pharmacokinetic Model.

Test compound is formulated immediately prior to dosing by dissolving in sterile 0.9 percent saline to a 5 mg/mL preparation. Dogs are given a single 2 mg/kg dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters: elimination rate constant, Ke; total clearance, Clt; volume of distribution, V$_D$; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Surgical preparation and instrumentation of the dogs are as described in Jackson, et al., *Circulation*, 82, 930–940 (1990). Mixed-breed hounds (aged 6–7 months, either sex, Butler Farms, Clyde, N.Y.) are anesthetized with sodium pentobarbital (30 mg/kg intravenously, i.v.), intubated, and ventilated with room air. Tidal volume and respiratory rates are adjusted to maintain blood PO$_2$, PCO$_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire)

3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-pA direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/hour is begun simultaneously with an infusion of thrombolytic agent (e.g. tissue plasminogen activator, streptokinase, APSAC). Reperfusion is followed for 3 hours after administration of test compound. Reocclusion of coronary arteries after successful thrombolysis is defined as zero CBF which persisted for at least 30 minutes.

Hematology and Template Bleeding Time Determinations

Whole blood cell counts, hemoglobin, and hematocrit values are determined on a 40-µL sample of citrated (3.8 percent) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time device (Organon Teknika Durham, N.C., U.S.A.). The device is used to make two horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Student-Neuman-Kuels post hoc t test to determine the level-of significance. Repeated-measures ANOVA are used to determine significant differences between time points during the experiments. Values are determined to be statistically different at least at the level of p<0.05. All values are mean±SEM. All studies are conducted in accordance with the guiding principles of the American Physiological Society. Further details regarding the procedures are described in Jackson, et al., *J. Cardiovasc. Pharmacol.*, (1993), 21, 587–599.

The following Examples are provided to further describe the invention and are not to be construed as limitations thereof.

The abbreviations, symbols and terms used in the examples have the following meanings.

Anal.=elemental analysis
Bn or Bzl=benzyl
Bu=butyl
Calcd=calculated
DMF=dimethylformamide
Et=ethyl
EtOH=ethanol
FAB=Fast Atom Bombardment (Mass Spectroscopy)
FDMS=field desorption mass spectrum
Hex=hexanes
HPLC=High Performance Liquid Chromatography
HRMS=high resolution mass spectrum
i-PrOH=isopropanol
IR=Infrared Spectrum
LAH=lithium aluminum hydride
Me=methyl
MeOH=methanol
MPLC=Medium Pressure Liquid Chromatography
NMR=Nuclear Magnetic Resonance
Ph=phenyl
i-Pr=isopropyl
Rochelle's Salt=potassium sodium tartrate
RPHPLC=Reversed Phase High Performance Liquid Chromatography
SiO$_2$=silica gel
TBS=tert-butyldimethylsilyl
TFA=trifluoroacetic acid
THF=tetrahydrofuran
TIPS=triisopropylsilyl
TLC=thin layer chromatography Unless otherwise stated, pH adjustments and work up are with aqueous acid or base solutions. PrepLC indicates preparative liquid chromatography using "Prep Pak™" silica cartridges; radial chromatography indicates preparative chromatography using a "Chromatotron™" instrument.

EXAMPLE 1

Preparation of 2-[2-(1-Pyrrolidinyl)ethoxy]-5-[3-[4-[2-(1-pyrrolidinyl)ethoxy]benzyl]benzo[b]thiophen-2-yl]benzoic Acid Sodium Salt

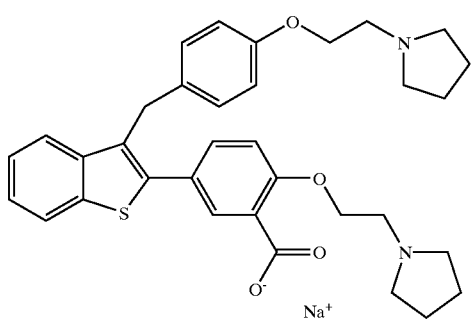

A. 2-[3-(1,3-Dioxolan-2-yl)-4-[2-(1-pyrrolidinyl)ethoxy]-phenyl]-α-[4-[2-(1-pyrrolidinyl)ethoxy]phenyl]-benzo[b]thiophene-3-methanol.

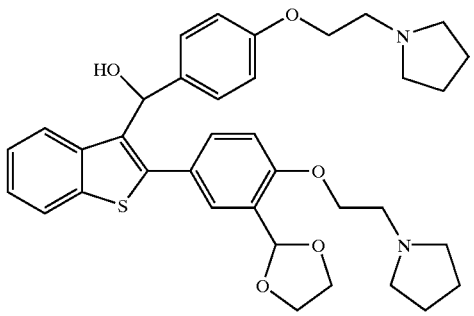

To a solution of 500 mg (0.966 mmol) of 2-[3-(1,3-dioxolan-2-yl)-4-hydroxyphenyl]-α-[4-[2-(1-pyrrolidinyl)ethoxy]phenyl]benzo[b]thiophene-3-methanol in 5.0 mL of dry DMF was added (1.25 g, 3.86 mmol) of cesium carbonate followed by addition of 1-(2-chloroethyl)pyrrolidine hydrochloride (181 mg, 1.06 mmol). The slurry was stirred at 80° C. for 2 h. The reaction mixture was then cooled to room temperature and diluted with 10 mL of water. The mixture was extracted with EtOAc. The combined organic layers were washed with brine and dried over MgSO$_4$. The filtrate was concentrated in vacuo and xylenes used as an azeotrope to remove residual DMF. Purification by flash chromatography (silica gel, 9% [10% conc. NH$_4$OH in MeOH] in CH$_2$Cl$_2$ afforded 500 mg (0.813 mmol, 84%) of the title product as a white foam.

mp 81–84° C.; FDMS 615 (M$^+$); Anal. for C$_{36}$H$_{42}$N$_2$O$_5$S: Calcd: C, 70.33; H, 6.89; N, 4.56; Found: C, 70.33; H, 6.77; N, 4.50.

B. 2-[2-(1-Pyrrolidinyl)ethoxy]-5-[3-[4-[2-(1-pyrrolidinyl)ethoxy]benzyl]benzo[b]thiophen-2-yl]benzaldehyde.

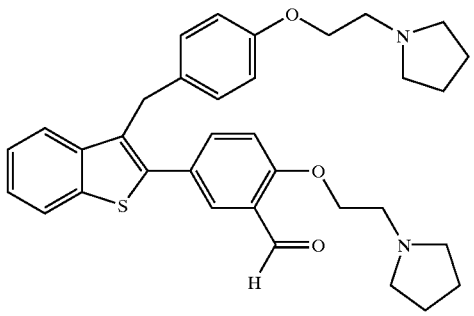

The title compound was prepared in 68% yield from the above carbinol (Part A) treating a solution of the carbinol in methylene chloride, cooled in an ice-water bath and under argon, with excess triethylsilane (about 7 equivalents), followed by the dropwise addition of TFA (about 10 equivalents). After 1 min, the reaction was quenched with saturated aqueous sodium bicarbonate; and the mixture was extracted with EtOAc. The extracts were washed with brine, dried with sodium sulfate, and evaporated to afford a residue which was purified by flash chromatography on silica gel, eluting with a gradient of EtOAc/Et$_3$N.

FDMS 555 (M$^+$); Anal. for C$_{34}$H$_{38}$N$_2$O$_3$S.0.75CH$_2$Cl$_2$: Calcd: C, 67.49; H, 6.44; N, 4.53; Found: C, 67.53; H, 6.67; N, 4.46.

C. Methyl 2-[2-(1-Pyrrolidinyl)ethoxy]-5-[3-[4-[2-(1-pyrrolidinyl)ethoxy]benzyl benzo[b]thiophen-2-yl]-benzoate.

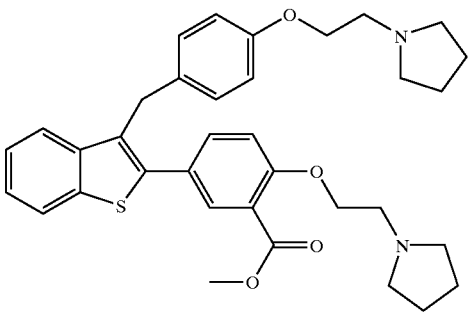

To a solution 270 mg (0.487 mmol) of 2-[2-(1-pyrrolidinyl)ethoxy]-5-[3-[4-[2-(1-pyrrolidinyl)ethoxy]benzyl]-benzo[b]thiophen-2-yl]benzaldehyde (Part B) in 5.0 mL of dry MeOH was added 5.40 mg (0.111 mmol) of sodium cyanide and 580 mg (4.87 mmol) of manganese(IV) oxide. The mixture was then heated at reflux for 2 h. The reaction mixture was cooled to room temperature and filtered through a pad of diatomaceous earth and washed with a mixture of EtOAc:CH$_2$Cl$_2$. The crude product was purified by chromatography (silica gel, 7% [2 M NH$_3$ in MeOH] in CH$_2$Cl$_2$ to yield 135 mg (0.231 mmol, 47%) of a light yellow semisolid.

$^1$HNMR (CDCl$_3$) δ 7.92 (d, J=2.4 Hz, 1H), 7.83 (m, 1H), 7.55 (d, J=8.6 Hz, 1H), 7.54 (d, J=8.8 Hz, 1H), 7.30 (m, 2H), 7.03 (d, J=8.6 Hz, 2H), 6.99 (d, J=8.8 Hz, 1H), 6.80 (d, J=8.7 Hz, 2H), 4.23 (t, J=6.1 Hz, 2H), 4.18 (s, 2H), 4.06 (t, J=6.0 Hz, 2H), 3.83 (s, 3H), 3.00 (t, J=6.1 Hz, 2H), 2.89 (t, J=6.0 Hz, 2H), 2.62–2.69 (m, 8H), 1.81 (m, 8H); FDMS 585 (M$^+$).

D. 2-[2-(1-Pyrrolidinyl)ethoxy]-5-[3-[4-[2-(1-pyrrolidinyl)ethoxy]benzyl]benzo[b]thiophen-2-yl]benzoic Acid Sodium Salt.

The title compound was prepared in 81% yield from methyl 2-[2-(1-pyrrolidinyl)ethoxy]-5-[3-[4-[2-(1-pyrrolidinyl)ethoxy]benzyl]benzo[b]thiophen-2-yl] benzoate (Part C) by saponification of a stirred solution (about 10% w/v) in 1:1 THF:MeOH with 1 N NaOH (1 equivalent) at room temperature (about 22 h). The reaction mixture was evaporated under reduced pressure and dried in a vacuum oven over P$_2$O$_5$ to provide the acid salt.

mp 253–255° C. (dec.); IR (KBR) 3400 (br), 1603, 1586 cm$^{-1}$; Ion Spray MS 571 (M+1)$^+$, 569 (M−1)$^-$; Anal. for C$_{34}$H$_{37}$N$_2$O$_4$S.1.0Na.0.8H$_2$O: Calcd: C, 67.26; H, 6.41; N, 4.61; Found: C, 66.92; H, 6.29; N, 4.52.

The phenolic starting material for Part A, above, was prepared as follows:

E. 2-[4-Trityloxy-3-(1,3-dioxolan-2-yl)phenyl]-benzo[b]thiophene.

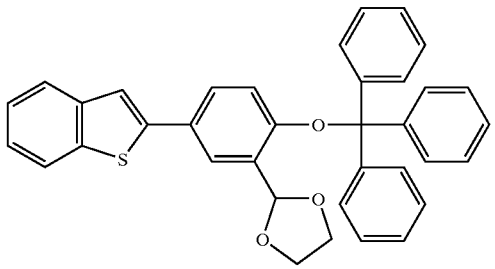

The title compound was prepared in 69% yield by coupling benzo[b]thiophene-2-boronic acid and 2-(5-bromo-2-trityloxyphenyl)-1,3-dioxolane using benzene, tetrakis-(triphenylphosphine)palladium(0) and 2.0 N sodium carbonate solution, vigorously stirred at 85° C. Following cooling and addition of brine, the layers were separated and the aqueous layer extracted with EtOAc. After drying and evaporation of the organic phase, the product was purified by chromatography.

FDMS 540 (M$^+$); base peak 243 (M−297); Anal. for C$_{36}$H$_{28}$O$_3$S: Calcd: C, 79.97; H, 5.22; Found: C, 79.76; H, 5.44.

F. 3-Bromo-2-[4-trityloxy-3-(1,3-dioxolan-2-yl)phenyl]-benzo[b]thiophene.

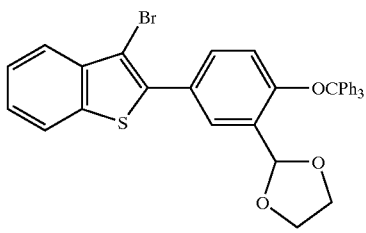

The title compound was prepared from the above benzothiophene in quantitative yield by treatment of a solution in CCl$_4$ with a slight excess NBS (about 1.1 equivalent) and AIBN (0.1 equivalent). The mixture was heated under reflux, cooled, filtered and concentrated under reduced pressure, followed by trituration with hexanes and filtration.

FDMS 620 (M$^+$); Anal. for C$_{36}$H$_{27}$BrO$_3$S.0.11CCl$_4$: Calcd: C, 68.14; H, 4.28; Found: C, 68.14; H, 4.31.

G. 2-[4-Trityloxy-3-(1,3-dioxolan-2-yl)phenyl]-benzo[b]thiophene-3-carboxaldehyde.

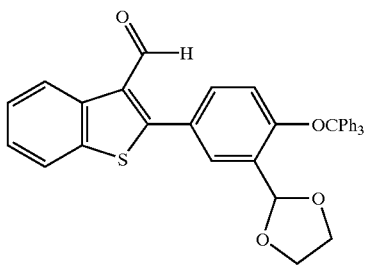

3-Bromo-2-[4-trityloxy-3-(1,3-dioxolan-2-yl)phenyl]-benzo[b]thiophene (Part F; 28.7 g, 46.2 mmol) was dissolved in 300 mL of freshly distilled THF and cooled to −78° C. To the solution was added 1.6 M n-BuLi in hexanes (34.7 mL, 55.5 mmol) dropwise over a period of 1 h. The dark brown solution was stirred at −78° C. for 1.5 h. Dry DMF (14.3 mL, 185 mmol) was then added dropwise over 20 min and the reaction mixture was slowly warmed to room temperature and stirred for 19 h. The reaction was quenched with 300 mL of satd NH$_4$Cl solution. The mixture was extracted (3×1 L) with EtOAc. The combined organic layers were dried over Na$_2$SO$_4$ and concentrated under reduced pressure. Purification by column chromatography on the PrepLC (silica gel, 0% to 6% to 10% EtOAc-Hexanes) afforded 6.70 g (11.8 mmol, 25%) of a white foam.

FDMS 243 (M−325); 325 (M−243); Anal. for C$_{37}$H$_{28}$O$_4$S.0.15CH$_2$Cl$_2$: Calcd: C, 76.74; H, 4.91; Found: C, 76.69; H. 5.15.

H. 2-[4-Trityloxy-3-(1,3-dioxolan-2-yl)phenyl]-α-[4-[2-(1-pyrrolidinyl)ethoxy]phenyl]benzo[b]thiophene-3-methanol.

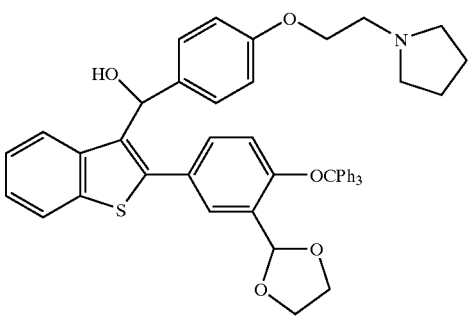

The title compound was prepared in 77% yield by treating 2-[4-trityloxy-3-(1,3-dioxolan-2-yl)phenyl]-benzo[b]thiophene-3-carboxaldehyde (Part G) with 4-[2-(1-pyrrolidinyl)ethoxy]phenyl magnesium bromide in THF at 0° C. The reaction was quenched at 0° C. with saturated aqueous NH$_4$Cl solution and extracted with EtOAc. The combined organic layers were dried (MgSO$_4$), evaporated and purified by flash chromatography.

$^1$HNMR (CDCl$_3$) δ 7.75 (d, J=7.8 Hz, 1H), 7.66 (d, J=7.7 Hz, 1H), 7.58 (d, J=2.3 Hz, 1H), 7.49 (d, J=7.1 Hz, 6H), 7.14–7.31 (m, 12H), 6.89–6.99 (m, 2H), 6.81 (d, J=8.7 Hz, 2H), 6.45 (d, J=8.6 Hz, 1H), 6.27 (s, 1H), 6.05 (s, 1H), 4.24 (t, J=5.3 Hz, 2H), 3.99 (m, 4H), 3.12 (dist t, 2H), 2.96 (m, 4H), 1.94 (m, 4H); FDMS 760 (M$^+$) base peak 243 (M−517).

I. 2-[4-Hydroxy-3-(1,3-dioxolan-2-yl)phenyl]-α-[4-[2-(1-pyrrolidinyl)ethoxy]phenyl]benzo[b]thiophene-3-methanol.

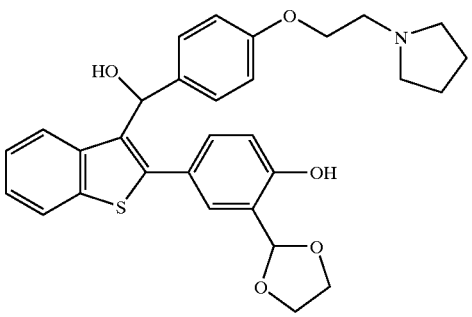

To a solution of (1.74 g, 2.29 mmol) of 2-[4-trityloxy-3-(1,3-dioxolan-2-yl)phenyl]-α-[4-[2-(1-pyrrolidinyl)ethoxy]phenyl]benzo[b]thiophene-3-methanol (Part H) in 23 mL of a THF-EtOH mixture (1:1 ratio) was added (0.50 mL, 4.57 mmol) of anisole followed by addition of 1.75 g of 10% Pd on carbon. The black slurry was stirred at room temperature under hydrogen (balloon pressure) for 24 h. The slurry was filtered through a pad of diatomaceous earth and rinsed with warm EtOH. The filtrate was concentrated. Purification by flash chromatography (silica gel, 7% to 9% [10% conc NH₄OH in MeOH]/CH₂Cl₂) afforded 954 mg (1.84 mmol, 81%) of a yellow foam.

¹HNMR (CDCl₃) δ 7.79 (d, J=8.0 Hz, 1H), 7.71 (d, J=7.9 Hz, 1H), 7.40 (d, J=2.2 Hz, 1H), 7.17–7.36 (m, 5H), 6.91 (d, J=8.4 Hz, 1H), 6.82 (d, J=8.6 Hz, 2H), 6.16 (s, 1H), 5.93 (s, 1H), 5.29 (s, 1H), 4.03–4.16 (m, 6H), 2.96 (dist t, 2H), 2.74 (m, 4H), 1.83 (m, 4H); FDMS 517 (M⁺).

EXAMPLE 2

Preparation of 2-(3-Carboxypropoxy)-5-[3-[4-[2-(1-pyrrolidinyl)ethoxy]benzyl]benzo[b]thiophen-2-yl] benzoic Acid Disodium Salt

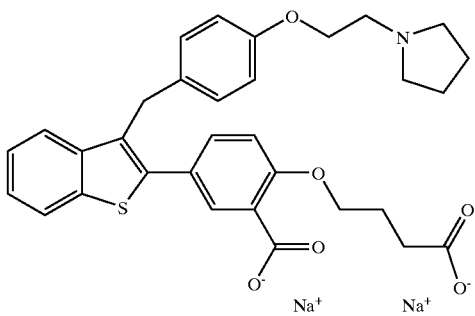

A. Methyl 2-(3-Carbomethoxypropoxy)-5-[3-[4-[2-(1-pyrrolidinyl)ethoxy]benzyl]benzo[b]thiophen-2-yl] benzoate.

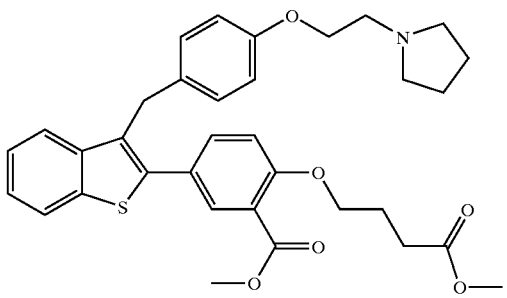

The title compound was prepared in 85% yield by essentially following the same procedure detailed in Example 1, Part C, from methyl 4-[2-formyl-4-[3-[4-[2-(1-pyrrolidinyl)ethoxy]benzyl]benzo[b]thiophen-2-yl]-phenoxy]butyrate.

IR (CHCl₃) 1729 cm⁻¹; ¹HNMR (CDCl₃) δ 7.93 (d, J=2.4 Hz, 1H), 7.84 (m, 1H), 7.53 (d, J=8.7 Hz, 1H), 7.52 (d, J=8.4 Hz, 1H), 7.31 (m, 2H), 7.03 (d, J=8.6 Hz, 2H), 6.98 (d, J=8.7 Hz, 1H), 6.79 (d, J=8.7 Hz, 2H), 4.21 (dist t, 2H), 4.18 (s, 2H), 4.12 (t, J=6.0 Hz, 2H), 3.85 (s, 3H), 3.68 (s, 3H), 3.08 (dist t, 2H), 2.89 (br m, 4H), 2.62 (t, J=7.2 Hz, 2H), 2. 16 (m, 2H), 1.92 (br m, 4H); FDMS 587 (M⁺).

B. 2-(3-Carboxypropoxy)-5-[3-[4-[2-(1-pyrrolidinyl)-ethoxy]benzyl]benzo[b]thiophen-2-yl]benzoic Acid Disodium Salt.

The title compound was prepared in 98% yield from methyl 2-(3-carbomethoxypropoxy)-5-[3-[4-[2-(1-pyrrolidinyl)ethoxy]benzyl]benzo[b]thiophen-2-yl] benzoate (Part A) by essentially following the procedure outlined in Example 1, Part D, (except using 2.0 equivalents of 1 N NaOH solution).

mp >250° C.; IR (KBR) 3425 (br), 1610, 1576 cm⁻¹; Ion Spray MS 560 (M+2)⁺, 558 (M⁻); Anal. for C₃₂H₃₁NO₆S.2Na.0.6H₂O: Calcd: C, 62.46; H, 5.29; N, 2.28; Found: C, 62.16; H, 5.15; N, 1.97.

The methyl 4-[2-formyl-4-[3-[4-[2-(1-pyrrolidinyl)-ethoxy]benzyl]benzo[b]thiophen-2-yl)phenoxy]butyrate starting material for Part A, above, was prepared as follows:

C. Methyl 4-[2-(1,3-Dioxolan-2-yl)-4-[3-[α-hydroxy-4-[2-(1-pyrrolidinyl)ethoxy]benzyl]benzo[b]thiophen-2-yl]-phenoxy]butyrate.

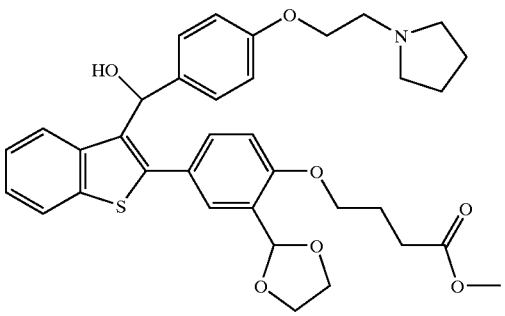

The title compound was prepared in 54% yield by essentially following the procedures outlined in above in Example 1, Part A, from the phenol of Example 1, Part I, above, and methyl 4-chlorobutyrate.

FDMS 618 (M⁺); Anal. for C₃₅H₃₉NO₇S: Calcd: C, 68.05; H, 6.36; N, 2.27; Found: C, 68.28; H, 6.58; N, 2.43.

D. Methyl 4-[2-Formyl-4-[3-[α-hydroxy-4-[2-(1-pyrrolidinyl)ethoxy]benzyl]benzo[b]thiophen-2-yl] phenoxy]butyrate.

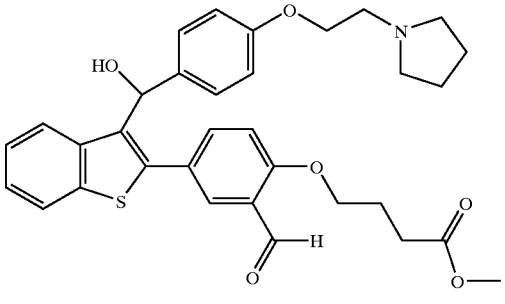

A solution of methyl 4-[2-(1,3-dioxolan-2-yl)-4-[3-[α-hydroxy-4-[2-(1-pyrrolidinyl)ethoxy]benzyl]benzo[b]-thiophen-2-yl]phenoxy]butyrate (160 mg, 0.259 mmol) in 2.6 mL of AcOH/H₂O mixture (4:1 ratio) was stirred at room temperature for 1 h 40 min. The reaction mixture was then concentrated under reduced pressure and azeotroped with benzene to afford 149 mg (0.259 mmol, quantitative yield) of an off-white foam.

FDMS 573 (M⁺); Anal. for C₃₃H₃₅NO₆S: Calcd: C, 69.09; H, 6.15; N, 2.44; Found: C, 68.84; H, 5.91; N, 2.57.

E. Methyl 4-[2-Formyl-4-[3-[4-[2-(1-pyrrolidinyl)-ethoxy]benzyl]benzo[b]thiophen-2-yl]phenoxy]butyrate.

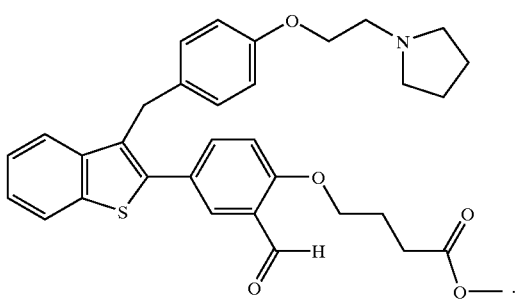

The title compound was prepared in 79% yield by essentially following the procedures outlined above in Example 1, Part B, from the above carbinol.

FDMS 558 (M$^+$); Anal. for $C_{33}H_{35}NO_5S$: Calcd: C, 71.07; H, 6.33; N, 2.51; Found: C, 70.79; H, 6.32; N, 2.22.

EXAMPLE 3

Preparation of Methyl 2-(3-Carbomethoxypropoxy)-5-[3-[4-[2-(1-pyrrolidinyl)ethoxy]benzyl]benzo[b]thiophen-2-yl]benzoate Oxalate Salt

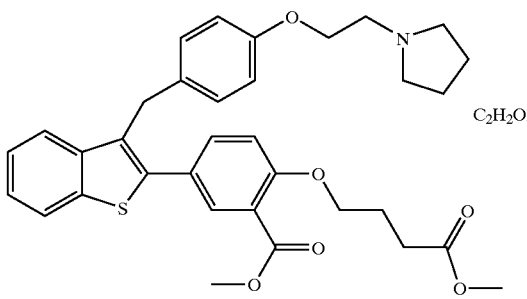

The title compound was prepared in quantitative yield from methyl 2-(3-carbomethoxypropoxy)-5-[3-(4-[2-(1-pyrrolidinyl)ethoxy]benzyl]benzo[b]thiophen-2-yl] benzoate (Example 2, Part A) by treating a solution of the diester in 3:1 EtOAc:CH$_2$Cl$_2$ with an equimolar amount of 0.5 M oxalic acid in EtOAc. The resulting slurry was stirred at room temperature about 2 h before it was concentrated in vacuo to provide the title product as a solid.

Ion Spray MS 588 (M$^+$); Anal. for $C_{34}H_{37}NO6S.0.84C_2H_2O_4$: Calcd: C, 64.60; H, 5.88; N, 2.11; Found: C, 64.58; H, 6.25; N, 2.11.

EXAMPLE 4

Preparation of 2-(3-Carbomethoxypropoxy)-5-[3-[4-[2-(1-pyrrolidinyl)ethoxy]benzyl]benzo[b]thiophen-2-yl]benzamide Oxalate Salt

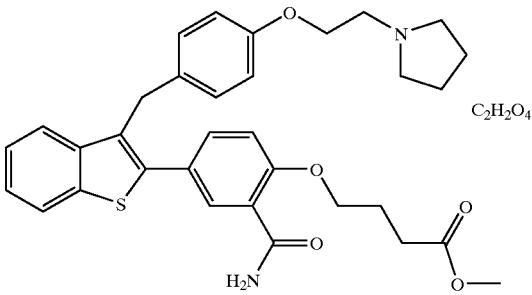

To a solution of 133 mg (0.238 mmol) methyl 4-[2-formyl-4-[3-[4-[2-(1-pyrrolidinyl)ethoxy]benzyl]-benzo[b]thiophen-2-yl]phenoxy]butyrate (Example 2, Part E) in 5.0 mL of 0.5 M ammonia in dioxane was added 58.2 mg (1.19 mmol) of sodium cyanide and two portions (286 mg each, 2.37 mmol each) of manganese(IV) oxide added 10 minutes apart. The black slurry was stirred for 22 h at room temperature, filtered through a pad of diatomaceous earth, and washed with THF. The filtrate was concentrated to dryness in vacuo. The residue was then purified by chromatography (silica gel, 5% [2 M ammonia in MeOH]/CH$_2$Cl$_2$) to yield 78.1 mg (0.136 mmol, 57%) of a white foam. The oxalate salt was prepared in quantitative yield by essentially following the procedure detailed in Example 3.

IR (free base) (KBR) 3485, 3385, 1734, 1670 cm$^{-1}$; Ion Spray MS 573 (M$^+$); Anal. for $C_{33}H_{36}N_2O_5S.0.68C_2H_2O_4$: Calcd: C, 65.10; H, 5.94; N, 4.42; Found: C, 65.05; H, 6.27; N, 4.61.

EXAMPLE 5

Preparation of 2-[2-(1-Pyrrolidinyl)ethoxy]-5-[6-hydroxy-3-[3-methoxy-4-[(1-pyrrolidinyl)methyl]benzyl]-benzo[b]thiophen-2-yl]benzoic Acid Sodium Salt

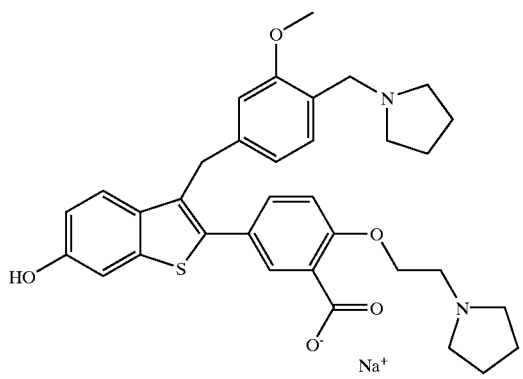

A. Preparation of 6-Isopropoxybenzo[b]thiophene-2-boronic Acid.

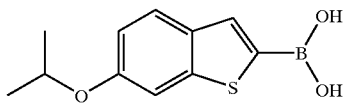

The title compound was prepared in 36% overall yield from 6-isopropoxybenzothiophene by essentially following the procedure detailed in WO 97/25033, Example 1, Part A.

FDMS 236 (M$^+$), Base peak 192 (M–44)$^+$; $^1$HNMR (CDCl$_3$) δ 8.19 (s, 1H), 7.83 (d, J=8.8 Hz, 1H), 7.39 (d, J=2.1 Hz, 1H), 7.02 (dd, J=8.8, 2.3 Hz, 1H), 4.66 (m, J=6.1 Hz, 1H), 1.41 (d, J=6.0 Hz, 6H).

B. 6-Isopropoxy-2-[4-trityloxy-3-(1,3-dioxolan-2-yl)-phenyl]benzo[b]thiophene.

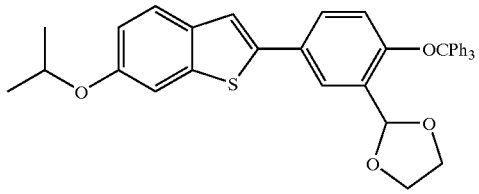

The title compound was prepared in 67% yield by essentially following the procedure detailed in WO 97/25033, Example 1, Part B from 6-isopropoxybenzo[b]thiophene-2-boronic acid (Part A) and 2-(5-bromo-2-trityloxyphenyl)-1,3-dioxolane.

FDMS 598 (M$^+$); Anal. for C$_{39}$H$_{34}$O$_4$S: Calcd: C, 78.23; H, 5.72; Found: C, 78.18; H, 5.67.

C. 3-Bromo-6-isopropoxy-2-[4-trityloxy-3-(1,3-dioxolan-2-yl)phenyl]benzo[b]thiophene.

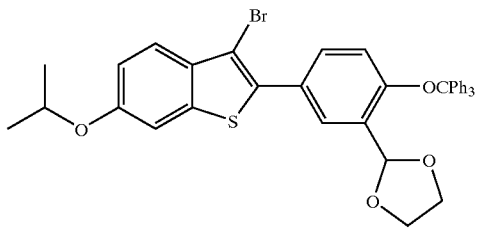

The title compound was prepared in quantitative yield by essentially following the procedure described above in Example 1, Part F from 6-isopropoxy-2-[4-trityloxy-3-(1,3-dioxolan-2-yl)phenyl]benzo[b]thiophene.

FDMS 678 (M$^+$), Base Peak 243 (M–435)$^+$; $^1$HNMR (CDCl$_3$) δ (7.85 (d, J=2.4 Hz, 1H), 7.65 (d, J=8.8 Hz, 1H), 7.52 (d, J=7.1 Hz, 6 H), 7.33–7.21 (m, 11H), 7.01 (dd, J=8.9, 2.3 Hz, 1H), 6.49 (d, J=8.7 Hz, 1H), 6.31 (s, 1H), 4.59 (m, J=6.1 Hz, 1H), 4.21–4.04 (m, 4H), 1.37 (d, J=6.0 Hz, 6H).

D. 2-[3-(1,3-Dioxolan-2-yl)-4-trityloxyphenyl]-3-formyl-6-isopropoxybenzo[b]thiophene.

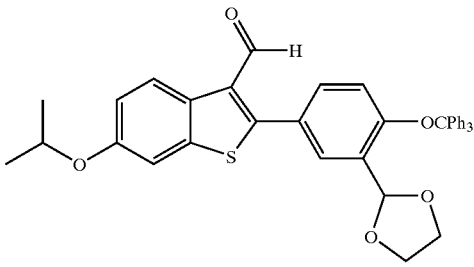

The title compound was prepared in 18% yield by essentially following the procedure detailed above in Example 1, Part G, from 3-bromo-6-isopropoxy-2-[4-trityloxy-3-(1,3-dioxolan-2-yl)phenyl]benzo[b]thiophene (Part C).

FDMS 626 (M$^+$), Base Peak 243 (M–384)$^+$; $^1$HNMR (CDCl$_3$) δ 9.81 (s, 1H), 8.57 (d, J=9.0 Hz, 1H), 7.68 (d, J=2.4 Hz, 1H), 7.51 (d, J=6.9 Hz, 6H), 7.33–7.23 (m, 10H), 7.05 (dd, J=9.0, 2.5 Hz, 1H), 7.02 (dd, J=8.8, 2.5 Hz, 1H), 6.52 (d, J=8.6 Hz, 1H), 6.28 (s, 1H), 4.61 (m, 1H), 4.18–4.06 (m, 4H), 1.37 (d, J=6.0 Hz, 6H).

E. 3-Bromo-6-methylanisole.

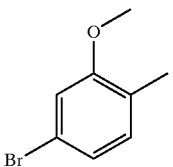

A solution of 5.00 g (30.1 mmol) of 3-methoxy-4-methylbenzoic acid dissolved in 40 mL of thionyl chloride was stirred at room temperature for 3.5 days. The resulting solution was evaporated to dryness in vacuo. The residual thionyl chloride was removed with benzene used as an azeotrope. The resulting crude acid chloride was then placed under high vacuum for 4 h. To a slurry of 4.80 g (33.1 mmol) of 1-hydroxypyridine-2-thione sodium salt in 180 mL of bromotrichloromethane was added 5.56 g (33.1 mmol) of the crude 3-methoxy-4-methylbenzoyl chloride and about 500 mg of AIBN dissolved in 120 mL of bromotrichloromethane. The mixture was stirred at reflux for 2 h. The mixture was then filtered and washed with CH$_2$Cl$_2$. The filtrate was concentrated in vacuo. The crude product was purified by flash chromatography (silica gel, 6% EtOAc in hexanes) to yield 2.86 g (14.2 mmol, 47%) of a yellow oil.

FDMS 200 (M$^+$); Anal. for C$_8$H$_9$BrO: Calcd: C, 47.79; H, 4.51; Found: C, 47.50; H, 4.36.

F. 1-(4-Bromo-2-methoxybenzyl)pyrrolidine.

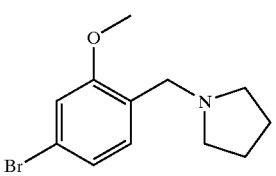

The title compound was prepared in 53% yield by using a similar procedure detailed in WO 97/25033, Example 37, Part A, from 3-bromo-6-methylanisole (Part E). Ion Spray MS 270 (M$^+$); Anal. for C$_{12}$H$_{16}$BrNO.0.6H$_2$O.0.3CH$_2$Cl$_2$: Calcd: C, 48.20; H, 5.85; N, 4.57; Found: C, 47.87; H, 5.47; N, 4.96.

G. 2-[3-(1,3-Dioxolan-2-yl)-4-trityloxyphenyl]-6-isopropoxy-α-[3-methoxy-4-(1-pyrrolidinylmethyl)phenyl]-benzo[b]thiophene-3-methanol.

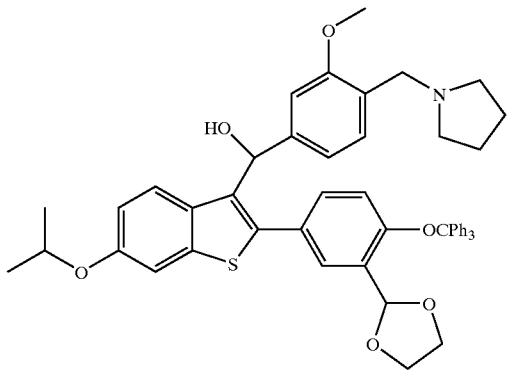

To a solution of 539 mg (1.99 mmol) of 1-(4-bromo-2-methoxy)benzylpyrrolidine (Part F) in 20 mL of dry THF cooled to −78° C. was added 1.37 mL (2.19 mmol) of 1.6 M n-BuLi in hexanes. The solution was stirred at −78° C. for 50 min. To the solution was added via cannula, 1.27 g (2.03 mmol) of 2-[3-(1,3-dioxolan-2-yl)-4-trityloxyphenyl]-3-formyl-6-isopropoxybenzo[b]thiophene (Part D) dissolved in 15 mL of THF. The acetone/dry ice bath was removed and the mixture was stirred for 2 h, 20 mL of satd. NH$_4$Cl solution was then added to quench the reaction. The mixture was extracted (2×250 mL) with EtOAc. The combined organic layers were dried over MgSO$_4$, filtered and concentrated. The crude product was purified by flash chromatography (silica gel, 7% [10% conc. NH4OH in MeOH]/CH$_2$Cl$_2$) to yield 1.4076 g (1.72 mmol, 86%) of an off-white foam.

IR 3437 (br) cm$^{-1}$; FDMS 819 (M$^+$), 576 (M−243)$^+$; Anal. for C$_{52}$H$_{51}$NO$_6$S.0.2NH$_5$O.0.1H$_2$O: Calcd: C, 75.53; H, 6.36; N, 2.03; Found: C, 75.21; H, 6.37; N, 2.06.

H. 2-[3-(1,3-Dioxolan-2-yl)-4-hydroxyphenyl]-6-isopropoxy-α-[3-methoxy-4-(1-pyrrolidinylmethyl)phenyl]-benzo[b]thiophene-3-methanol.

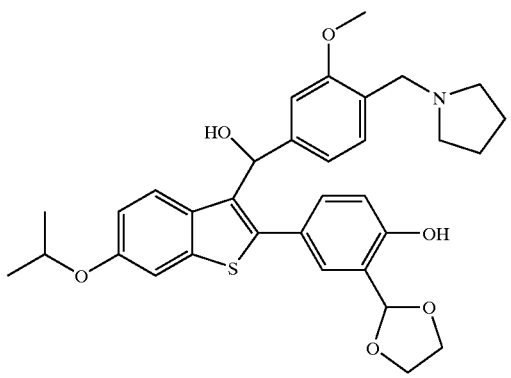

The title compound was prepared in 65% yield by essentially following the procedures detailed above in Example 1, Part I from 2-[3-(1,3-dioxolan-2-yl)-4-trityloxyphenyl]-6-isopropoxy-α-[3-methoxy-4-(1-pyrrolidinylmethyl)-phenyl]benzo[b]thiophene-3-methanol (Part G).

IR 3403 (br) cm$^{-1}$; Ion Spray MS 576 (M)$^+$, 575 (M−1)$^-$; Anal. for C$_{33}$H$_{37}$NO$_6$S.0.1NH$_4$OH: Calcd: C, 68.43; H, 6.53; N, 2.66; Found: C, 68.31; H, 6.57; N, 3.06.

I. 2-[3-(1,3-Dioxolan-2-yl)-4-[2-(1-pyrrolidinyl)ethoxy]-phenyl]-6-isopropoxy-α-[3-methoxy-4-(1-pyrrolidinylmethyl)-phenyl]benzo[b]thiophene-3-methanol.

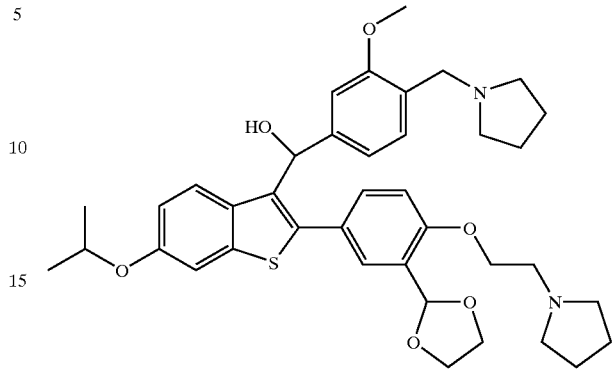

The title compound was prepared in 90% yield by essentially following the procedure detailed in Example 1, Part A, from 2-[3-(1,3-dioxolan-2-yl)-4-hydroxyphenyl]-6-isopropoxy-α-[3-methoxy-4-(1-pyrrolidinylmethyl)phenyl]-benzo[b]thiophene-3-methanol (Part H).

FDMS 672 (M$^+$); Anal. for C$_{39}$H$_{48}$N$_2$O$_6$S: Calcd: C, 69.62; H, 7.19; N, 4.16; Found: C, 69.82; H, 7.40; N, 4.32.

J. Methyl 5-[6-Isopropoxy-3-[3-methoxy-4-(1-pyrrolidinylmethyl)benzyl]benzo[b]thiophen-2-yl]-2-[2-(1-pyrrolidinyl)ethoxy]benzoate.

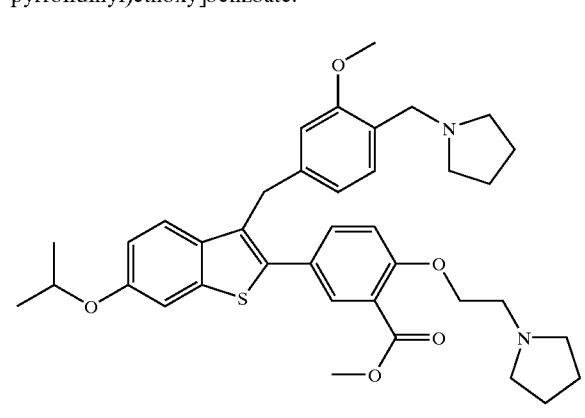

A solution containing 622 mg (0.924 mmol) of 2-[3-(1,3-dioxolan-2-yl)-4-[2-(1-pyrrolidinyl)ethoxy]phenyl]-6-isopropoxy-α-[3-methoxy-4-(1-pyrrolidinylmethyl)phenyl]-benzo[b]thiophene-3-methanol (Part I) in 9.2 mL of 4:1 HOAc:H$_2$O mixture was stirred at room temperature for 4 h. The solution was then concentrated to dryness in vacuo and the residual HOAc was removed with benzene used as an azeotrope. The resulting foam was then placed under reduced pressure for 2 h to yield 581 mg (0.924 mmol, quantitative yield) of the crude benzaldehyde. To a solution of 581 mg (0.9237 mmol) of the above benzaldehyde in 14 mL of dry CH$_2$Cl$_2$ cooled to 0° C. was added 1.03 mL (6.47 mmol) of triethylsilane followed by dropwise addition of 0.64 mL (8.31 mmol) of trifluoroacetic acid. The solution was stirred at 0° C. for 2 h. The ice bath was removed and the solution stirred at room temperature for an additional 2 h. The reaction was quenched with addition of 14 mL satd. NaHCO$_3$ soln. The mixture was extracted (2×75 mL) with CH$_2$Cl$_2$. The combined organic layers were dried over MgSO$_4$, filtered and concentrated in vacuo. The crude product was purified by flash chromatography (silica gel, 75:22:3 THF:Hexanes:Et₃N) to yield 168 mg (0.268 mmol, 29%) of the benzoic acid (obtained upon air oxidation of the deoxygenated benzaldehyde). To a solution containing 168 mg (0.268 mmol) of the benzoic acid in 5 mL of MeOH was added 25 drops of 3 M H₂SO₄. The solution was stirred at reflux for 4 days. The solution was cooled and concentrated to a volume of about 2 mL in vacuo. The residue was diluted in EtOAc and basified with 20 mL of satd. NaHCO₃. The layers were separated and the aqueous layer was extracted (1×30 mL) with EtOAc. The combined organic layers were dried over MgSO₄, filtered and concentrated in vacuo. The crude product was purified by flash chromatography (silica gel, 6% [2 M NH₃ in MeOH]/CH₂Cl₂) to yield 135.3 mg (0.210 mg, 79%, 23% overall from the acetal) of a light yellow foam.

IR 1725 cm⁻¹; Ion Spray MS 643 (M⁺), 674 (M+31)⁻; ¹HNMR (CDCl₃) δ 7.83 (d, J=2.2 Hz, 1H), 7.46 (dd, J=8.6, 2.5 Hz, 1H), 7.30 (d, J=8.6 Hz, 1H), 7.23 (d, J=2.2 Hz, 1H), 7.13 (d, J=7.3 Hz, 1H), 6.92–6.79 (m, 2H), 6.61 (d, J=7.7 Hz, 1H), 6.57 (s, 1H), 4.54–4.45 (m, 1H), 4.18–4.10 (m, 4H), 3.76 (s, 3H), 3.62 (s, 3H), 3.57 (s, 2H), 2.90 (t, J=6.1 Hz, 2H), 2.60–2.40 (m, 8H), 1.75–1.60 (m, 8H), 1.29 (d, J=6.2 Hz, 6H).

K. Methyl 5-[6-Hydroxy-3-[3-methoxy-4-(1-pyrrolidinylmethyl)benzyl]-2-[2-(1-pyrrolidinyl)ethoxy]benzo[b]thiophen-2-yl]benzoate.

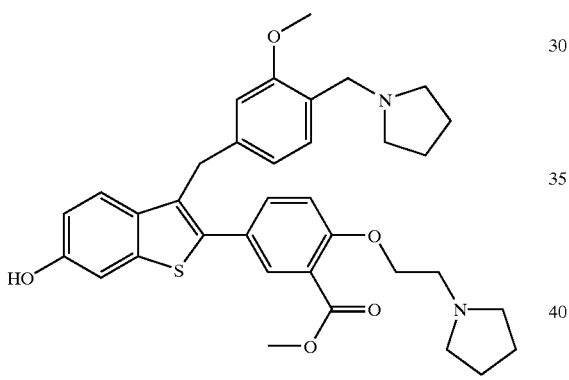

To a solution containing 86.1 mg (0.120 mmol) of methyl 5-[6-isopropoxy-3-[3-methoxy-4-(1-pyrrolidinylmethyl)-benzyl]benzo[b]thiophen-2-yl]-2-[2-(1-pyrrolidinyl)ethoxy]-benzoate dihydrochloride (prepared from free base of Part J) in 2.5 mL dry CH₂Cl₂ was added 0.60 mL of 1 M boron trichloride in CH₂Cl₂ at 0° C. The heterogeneous mixture was stirred at 0° C. for 45 min. To the mixture was added 0.75 mL of MeOH and the solution was stirred for an additional 45 min. at 0° C. The reaction was quenched with 3 mL of satd. NaHCO₃ soln. and the layers were separated. The aqueous layer was extracted (1×20 mL) with CH₂Cl₂. The combined organic layers were dried over MgSO₄, filtered and concentrated in vacuo. The crude product was purified by flash chromatography (silica gel, 8% [10% conc. NH₄OH in MeOH]/CH₂Cl₂) to afford 6.5 mg (0.011 mmol, 9%) of a yellow solid.

Ion Spray MS 601 (M⁺), 599 (M−1)⁻; ¹HNMR (CDCl₃) δ 7.86 (d, J=2.3 Hz, 1H), 7.34 (d, J=8.6 Hz, 1H), 7.27 (d, J=8.3 Hz, 1H), 7.21 (d, J=7.7 Hz, 1H), 7.01 (s, 1H), 6.77 (d, J=8.7 Hz, 1H), 6.68 (d, J=8.7 Hz, 1H), 6.64 (d, J=9.6 Hz, 1H), 6.60 (s, 1H), 4.19 (t, J=5.3 Hz, 2H), 4.10 (s, 2H), 3.84 (s, 2H), 3.81 (s, 3H), 3.60 (s, 3H), 3.04 (dist t, 2H), 2.82 (m, 8H), 1.87 (m, 8H).

L. 5-[6-Hydroxy-3-[3-methoxy-4-(1-pyrrolidinylmethyl)-benzyl]-2-[2-(1-pyrrolidinyl)ethoxy]benzo[b]thiophen-2-yl]-benzoic Acid Sodium Salt.

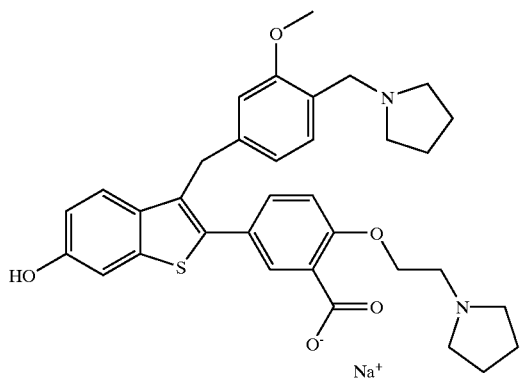

The title compound was prepared in quantitative yield by essentially following the procedures detailed above in Example 1, Part D, from methyl 5-[6-hydroxy-3-[3-methoxy-4-(1-pyrrolidinylmethyl)benzyl]-2-[2-(1-pyrrolidinyl)ethoxy]-benzo[b]thiophen-2-yl]benzoate (Part K).

Ion Spray MS 587 (M+1)⁺, 586 (M⁻); ¹HNMR (CD₃OD) δ 7.57 (s, 1H), 7.38 (d, J=7.8 Hz, 1H), 7.35 (d, J=8.0 Hz, 1H), 7.18 (s, 1H), 7.11 (d, J=7.8 Hz, 1H), 7.03 (d, J=7.9 Hz, 1H), 6.76 (d, J=7.3 Hz, 1H), 6.74 (s, 1H), 6.63 (d, J=8.0 Hz, 1H), 4.28–4.17 (m, 4H), 3.68 (s, 3H), 3.63 (s, 2H), 3.03 (m, 2H), 2.82 (m, 4H), 2.58 (m, 4H), 1.85–1.65 (m, 8H).

EXAMPLE 6

Preparation of 2-[[3-(3-Ethoxycarbonyl)propoxy]-4-[2-(1-pyrrolidinyl)ethoxy]phenyl]-3-[4-[2-(2-oxopyrrolidin-1-yl)-ethoxy]benzyl]benzo[b]thiophene Oxalate

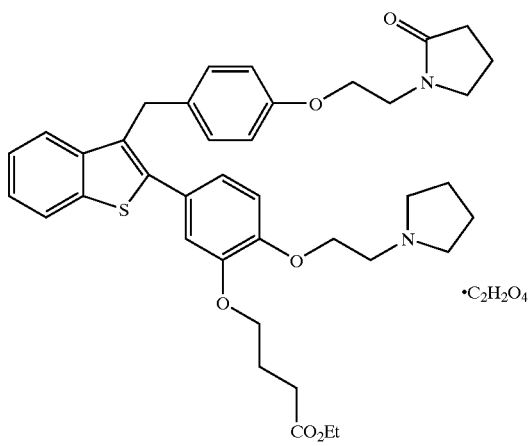

A. 4-Bromo-2-methoxyphenyl 2-(1-Pyrrolidinyl)ethyl Ether.

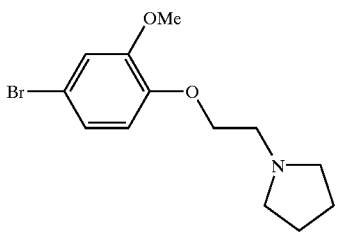

4-Bromoguaiacol (4-bromo-2-methoxyphenol: 30 g, 147.8 mmol) and 1-(2-chloroethyl)pyrrolidine HCl (37.7 g, 221.6 mmol) were heated at 80° C. in 500 mL of DMF in the presence of $K_2CO_3$ (61.3 g, 443.3 mmol) for 20 h. After cooling, the crude product was filtered and concentrated in vacuo. The crude residue was purified by flash chromatography ($SiO_2$; gradient of 0–2% TEA in EtOAc) to afford 27.7 g (92.3 mmol; 62%) of the title compound as a clear, colorless oil.

FDMS 299 (M−1), 301 (M+1); Anal. for $C_{13}H_{18}BrNO_2$: Calcd: C, 52.01; H, 6.04; N, 4.67; Found: C, 52.24; H, 5.97; N, 4.62.

B. 2-[3-Methoxy-4-[2-(1-pyrrolidinyl)ethoxy]phenyl]-benzo[b]thiophene.

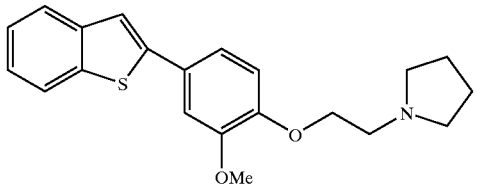

A solution of benzo[b]thiophene-2-boronic acid (18 g, 101.1 mmol) and 4-bromo-2-methoxyphenyl 2-(1-pyrrolidinyl)-ethyl ether (27.6 g, 91.9 mmol) in 500 mL of THF was treated with $Pd(PPh_3)_4$ (5 g, 4.3 mmol) and 96 mL of 2 N aqueous $Na_2CO_3$. The resulting mixture was heated overnight at 60° C. in the dark. Upon cooling to room temperature, the organic layer was decanted away from the solids, which were rinsed with THF (3×100 mL). The combined organic layers were concentrated in vacuo. Purification of the crude residue by flash chromatography ($SiO_2$; gradient of 0–2% TEA in EtOAc) gave quantitative yield of the title compound as a light tan solid.

FDMS 353 ($M^+$); Anal. for $C_{21}H_{23}NO_2S.0.2H_2O$: Calcd: C, 70.63; H, 6.61; N, 3.92; Found: C, 70.69; H, 6.52; N, 4.12.

C. 2-[3-Hydroxy-4-[2-(1-pyrrolidinyl)ethoxy]phenyl]-benzo[b]thiophene.

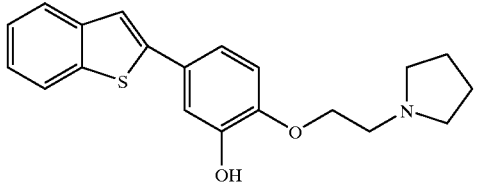

A 0° C. solution of 2-[3-methoxy-4-[2-(1-pyrrolidinyl)-ethoxy]phenyl]benzo[b]thiophene (32 g, 91.9 mmol) in 500 mL of dichloroethane was treated with $BBr_3$ (92 g, 369.6 mmol) dropwise via a dropping funnel. After 1.5 h, the reaction mixture was slowly poured into 1 L saturated aqueous $NaHCO_3$/ice. The layers were separated, and the aqueous layer was extracted with 5% MeOH/$CHCl_3$ (5×200 mL). The brown solid boron complex was stirred in 200 mL of 1 N HCl. The acidic solution was neutralized with NaOH and extracted with EtOAc (4×150 mL). The combined organic layers were dried over $K_2CO_3$, filtered and concentrated in vacuo. The crude residue was purified by flash chromatography ($SiO_2$; 1% MeOH in $CHCl_3$, saturated with $NH_4OH$) to give 8.01 g (23.7 mmol, 26%) of the title phenol as an off-white solid.

ISMS 338 (M−1), 340 (M+1); Anal. for $C_{20}H_{21}NO_2S.0.5H_2O$: Calcd: C, 68.94; H, 6.36; N, 4.02; Found: C, 68.88; H, 6.23; N, 4.20.

D. 4-Fluorophenyl 2-[3-(4-Fluorobenzoyloxy)-4-[2-(1-pyrrolidinyl)ethoxy]phenyl]benzo[b]thiophen-3-yl Ketone.

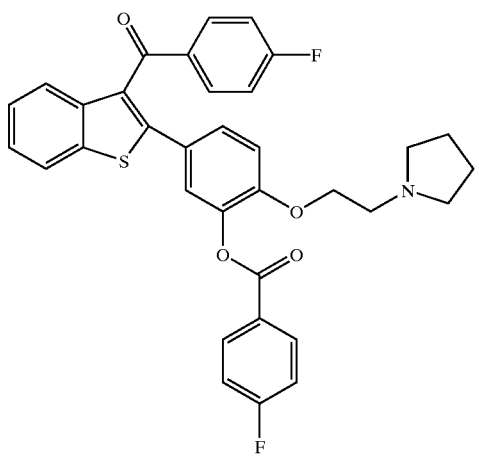

A 0° C. solution of 2-[3-hydroxy-4-[2-(1-pyrrolidinyl)-ethoxy]phenyl]benzo[b]thiophene (6.7 g, 19.8 mmol) in 200 mL of dichloroethane was treated with 4-fluorobenzoyl chloride (2.6 mL, 21.8 mmol) dropwise. A white precipitate formed. The reaction mixture was warmed to ambient temperature and stirred for 6.5 h. The intermediate ester was cooled to 0° C. and treated with 4-fluorobenzoyl chloride (2.6 mL, 21.8 mmol) and $TiCl_4$ (8.7 mL, 79.2 mmol). The reaction mixture was allowed to warm to ambient temperature. After 5 h, the reaction mixture was slowly poured into 200 mL saturated aqueous $NaHCO_3$. The layers were separated, and the aqueous layer was extracted with $CHCl_3$ (4×100 mL). The combined organic layers were dried over $K_2CO_3$, filtered and concentrated in vacuo. Purification of the crude residue by PrepLC ($SiO_2$; gradient of 100% $CHCl_3$ to 0.5% MeOH in $CHCl_3$, saturated with $NH_4OH$) afforded 7.5 g (12.9 mmol, 65%) of the title compound as a yellow foam.

ISMS 584 (M+1); Anal. for $C_{34}H_{27}F_2NO_4S.H_2O$: Calcd: C, 67.87; H, 4.86; N, 2.33; Found: C, 67.87; H, 4.82; N, 2.41.

E. 2-[3-Hydroxy-4-[2-(1-pyrrolidinyl)ethoxy]phenyl]-benzo[b]thiophen-3-yl 4-[2-(2-Oxopyrrolidin-1-yl)ethoxy]-phenyl] Ketone.

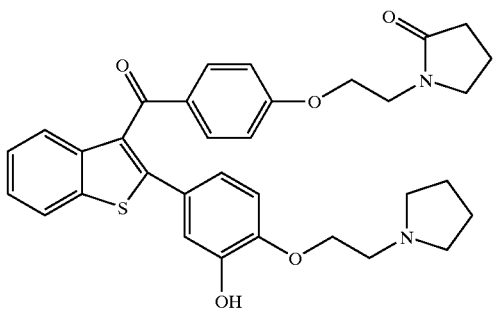

A 0° C. solution of 4-fluorophenyl 2-[3-(4-fluorobenzoyloxy)-4-[2-(1-pyrrolidinyl)ethoxy]phenyl]-benzo[b]thiophen-3-yl ketone (7.0 g, 12.0 mmol) and NaH (1.1 g, 26.4 mmol) in 60 mL of DMF was treated with 1-(2-hydroxyethyl)pyrrolidin-2-one (2.85 mL, 25.2 mmol) dropwise. After 30 min the reaction mixture was warmed to ambient temperature and allowed to stir overnight. The reaction mixture was poured into 150 mL of brine, and the aqueous layer was extracted with EtOAc (4×100 mL). The combined organic layers were washed with $H_2O$ (2×300 mL) dried over $K_2CO_3$, filtered and concentrated in vacuo. Purification of the crude residue by PrepLC ($SiO_2$; gradient of 0–2% MeOH/$CHCl_3$, saturated with $NH_4OH$) afforded 5.35 g (9.37 mmol, 78%) of the title compound. A small sample of the title ketone was converted to its oxalate salt.

FDMS 571 (M+1); Anal. for $C_{33}H_{34}N_2O_5S.C_2H_2O_4.0.1H_2O$: Calcd: C, 63.45; H, 5.51; N, 4.23; Found: C, 63.18; H, 5.87; N, 4.62.

F. 2-[3-Hydroxy-4-[2-(1-pyrrolidinyl)ethoxy]phenyl]-3-[2-(2-oxopyrrolidin-1-yl)ethoxy]benzyl]benzo[b]thiophene.

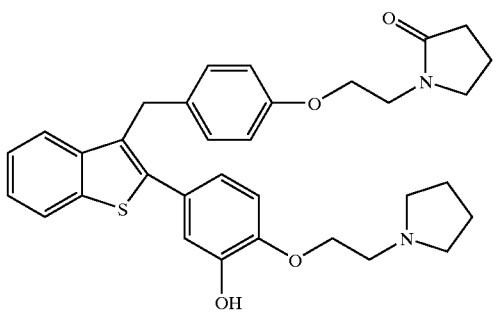

A ±35° C. solution of 2-[3-hydroxy-4-[2-(1-pyrrolidinyl)ethoxy]phenyl]benzo[b]thiophen-3-yl 4-[2-(2-oxopyrrolidin-1-yl)ethoxy]phenyl] ketone (5.0 g, 8.76 mmol) in 50 mL of THF was treated with LAH (1 M in THF, 8.8 mL, 8.76 mmol) dropwise. After 3 h the reaction mixture was quenched cold with 10 mL of $H_2O$. EtOAc and saturated aqueous Rochelle's salt (50 mL each) were added. The layers were separated, and the aqueous layer was extracted with EtOAc (4×50 mL). The combined organic layers were dried over $K_2CO_3$, filtered and concentrated in vacuo. Purification of the crude residue by PrepLC ($SiO_2$; gradient of 0.5–1% MeOH/$CHCl_3$, saturated with $NH_4OH$) afforded 4.0 g of the intermediate alcohol which was immediately dissolved in 50 mL of dichloroethane. The resulting solution was treated with $Et_3SiH$ (9.8 mL, 61.3 mmol). Upon cooling to 0° C., TFA (6.7 mL, 87.6 mmol) was added dropwise. After 1 h, the reaction mixture was poured into 150 mL of saturated aqueous $NaHCO_3$. The layers were separated, and the aqueous layer was extracted with $CHCl_3$ (3×50 mL). The combined organic layers were dried over $K_2CO_3$, filtered and concentrated in vacuo. Purification of the crude residue by flash chromatography ($SiO_2$; gradient of 1–2% MeOH/$CHCl_3$, saturated with $NH_4OH$) afforded 3.3 g (5.93 mmol, 68%) of the title compound, of which a small sample was converted to its oxalate salt.

FDMS 557 (M+1); Anal. for $C_{33}H_{36}N_2O_4S.C_2H_2O_4$: Calcd: C, 65.00; H, 5.92; N, 4.33; Found: C, 64.73; H, 6.13; N, 4.54.

G. 2-[[3-(3-Ethoxycarbonyl)propoxy]-4-[2-(1-pyrrolidinyl)ethoxy]phenyl]-3-[4-[2-(2-oxopyrrolidin-1-yl)ethoxy]-benzyl]benzo[b]thiophene Oxalate.

A slurry of 2-[3-hydroxy-4-[2-(1-pyrrolidinyl)ethoxy]-phenyl]-3-[2-(2-oxopyrrolidin-1-yl)ethoxy]benzyl]-benzo[b]thiophene (1.0 g, 1.8 mmol), ethyl 4-bromobutyrate (0.285 mL, 2.0 mmol) and $Cs_2CO_3$ (1.8 g, 5.5 mmol) in 10 mL of DMF was heated at 80° C. for 3 h. EtOAc and $H_2O$ (30 mL each) were added. The layers were separated, and the aqueous layer was extracted with EtOAc (2×50 mL). The combined organic layers were washed with $H_2O$ (3×50 mL), dried over $K_2CO_3$, filtered and concentrated in vacuo. Purification of the crude residue by radial chromatography ($SiO_2$; gradient of 1–2% MeOH/$CHCl_3$, saturated with $NH_4OH$) afforded 1.0 g (1.49 mmol, 83%) of the title compound, of which a small sample was converted to the oxalate salt.

FDMS 671 (M+1); Anal. for $C_{39}H_{46}N_2O_6S.0.6C_2H_2O_4.1.7H_2O$: Calcd: C, 63.91; H, 6.75; N, 3.71; Found: C, 63.51; H, 6.42; N, 4.10.

EXAMPLE 7

Preparation of 2-[3-(3-Carboxypropoxy)-4-[2-(1-pyrrolidinyl)ethoxy]phenyl]-3-[4-[2-(2-oxopyrrolidin-1-yl)ethoxy]-benzyl]benzo[b]thiophene Lithium Salt

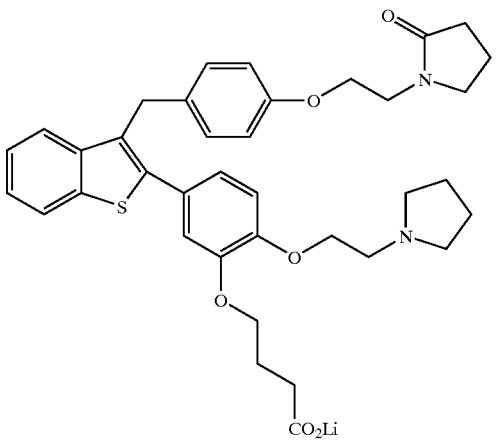

A solution of 2-[[3-(3-ethoxycarbonyl)propoxy]-4-[2-(1-pyrrolidinyl)ethoxy]phenyl]-3-[4-[2-(2-oxopyrrolidin-1-yl)ethoxy]benzyl]benzo[b]thiophene (Example 6, Part G; 300 mg, 0.447 mmol) in 5 mL of THF/MeOH/$H_2O$ (3:1:1) was treated with LiOH (11 mg, 0.459 mmol). After 6 h the reaction mixture was concentrated in vacuo to a white foam. The residue was dissolved in 2 mL of H2O and freeze-dried overnight to give 281 mg (0.433 mmol, 97%) of the title lithium salt.

FDMS 649 (M+1+Li), 655 (M+1+2Li); Anal. for C₃₇H₄₁LiN₂O₆S: Calcd: C, 68.50; H, 6.37; N, 4.32; Found: C, 68.22; H, 6.21; N, 4.17.

EXAMPLE 8

Preparation of 2-[3-(4-Amino-4-oxobutoxy)-4-[2-(1-pyrrolidinyl)ethoxy]phenyl]-3-[4-[2-(2-oxopyrrolidin-1-yl)ethoxy]-benzyl]benzo[b]thiophene Oxalate

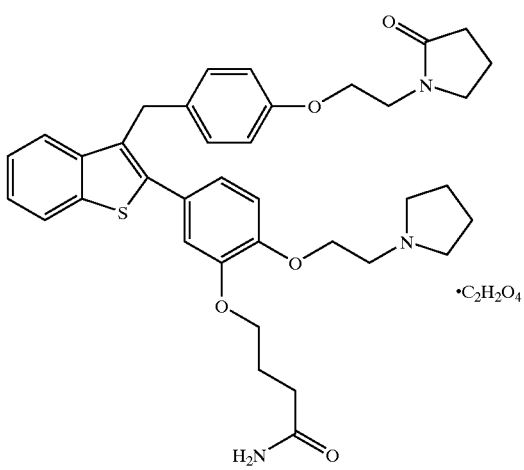

A −0° C. slurry of NH₄Cl (0.785 mL, 1.57 mmol) in 5 mL of toluene was treated with Me₃Al (2 M in THF, 0.785 mL, 1.57 mmol) dropwise via a syringe. The resulting mixture was allowed to warm to ambient temperature and stir for 45 min. A solution of 2-[[3-(3-ethoxycarbonyl)propoxy]-4-[2-(1-pyrrolidinyl)ethoxy]phenyl]-3-[4-[2-(2-oxopyrrolidin-1-yl)ethoxy]benzyl]benzo[b]thiophene (Example 6, Part G; 300 mg, 0.447 mmol) in 5 mL of toluene was added, and the reaction temperature was raised to 50° C. After 4 h, the reaction mixture was cooled to ambient temperature, quenched with 5 mL of 0.1 N HCl and basified with 0.1 N NaOH. The layers were separated, and the aqueous layer was extracted with CHCl₃ (3×25 mL). The combined organic layers were dried over K₂CO₃, filtered and concentrated in vacuo. Purification of the crude residue by radial chromatography (SiO₂; gradient of 1–2% MeOH/CHCl₃, saturated with NH₄OH) afforded 119 mg (0.185 mmol, 41%) of the title compound, which was converted to its oxalate salt.

ISMS 642 (M+1); Anal. for C₃₇H₄₃N₃O₅S·C₂H₂O₄·0.1H₂O: Calcd: C, 62.47; H, 6.32; N, 5.60; Found: C, 62.54; H, 6.35; N, 5.46.

EXAMPLE 9

Preparation of 2-[3-(4-Hydroxybutoxy)-4-[2-(1-pyrrolidinyl)ethoxy]phenyl]-3-[4-[2-(2-oxopyrrolidin-1-yl)ethoxy]-benzyl]benzo[b]thiophene Oxalate

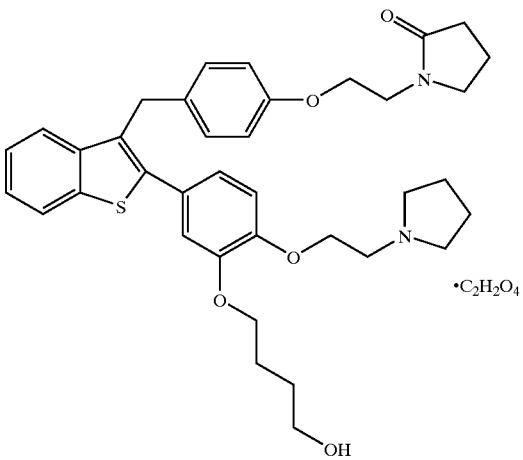

A −10° C. solution of 2-[[3-(3-ethoxycarbonyl)propoxy]-4-[2-(1-pyrrolidinyl)ethoxy]phenyl]-3-[4-[2-(2-oxopyrrolidin-1-yl)ethoxy]benzyl]benzo[b]thiophene (Example 6, Part G; 180 mg, 0.268 mmol) in 5 mL of THF was treated with LAH (1 M in THF, 0.27 mL, 0.268 mmol) dropwise. After 2 h, the reaction mixture was quenched cold with 1 mL of H₂O. EtOAc and saturated aqueous Rochelle's salt (20 mL each) were added. The layers were separated, and the aqueous layer was extracted with EtOAc (2×20 mL). The combined organic layers were dried over K₂CO₃, filtered and concentrated in vacuo. Purification of the crude residue by radial chromatography (SiO₂; gradient of 1–3% MeOH/CHCl₃, saturated with NH₄OH) afforded 38 mg (0.060 mmol, 23%) of the title compound, which was converted to its oxalate salt.

ISMS 629 (M+1); Anal. for C₃₇H₄₄N₂O₅S·1.5C₂H₂O₄·1.5H₂O: Calcd: C, 60.74; H, 6.37; N, 3.54; Found: C, 60.59; H, 6.23; N, 3.75.

EXAMPLE 10

Preparation of 2-[[3-(3-Ethoxycarbonyl)propoxy]-4-[2-(1-pyrrolidinyl)ethoxy]phenyl]benzo[b]thiophen-3-yl 4-[2-(2-Oxopyrrolidin-1-yl)ethoxy]phenyl] Ketone Oxalate

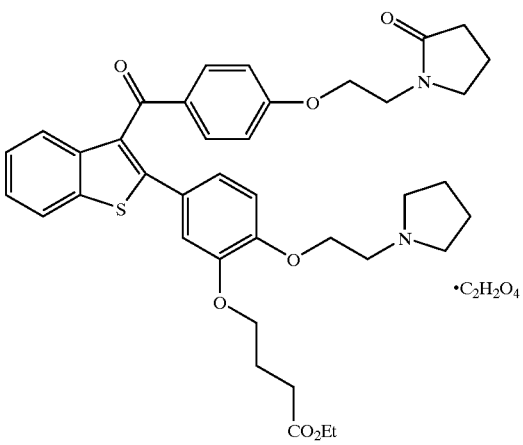

The title compound was prepared in 91% yield from 2-[3-hydroxy-4-[2-(1-pyrrolidinyl)ethoxy]phenyl]benzo[b]thiophen-3-yl 4-[2-(2-oxopyrrolidin-1-yl)ethoxy]phenyl] ketone (Example 6, Part E) according to the procedure detailed in Example 6, Part G.

FDMS 685 (M+1); FAB HRMS calcd for $C_{39}H_{45}N_2O_7S$: 685.2948. Found: 685.2952 (M+1); IR (KBr) 3446 (br), 1730, 1656, 1600.

EXAMPLE 11

Preparation of 2-[3-(3-Carboxypropoxy)-4-[2-(1-pyrrolidinyl)ethoxy]phenyl]benzo[b]thiophen-3-yl 4-[2-(2-Oxopyrrolidin-1-yl)ethoxy]phenyl] Ketone Lithium Salt

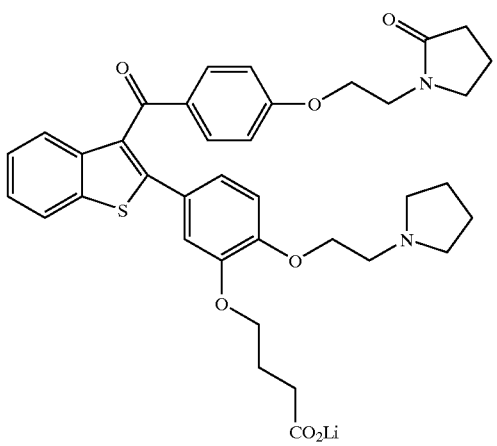

The title compound was prepared in 90% yield from 2-[[3-(3-ethoxycarbonyl)propoxy]-4-[2-(1-pyrrolidinyl) ethoxy]phenyl]-benzo[b]thiophen-3-yl 4-[2-(2-oxopyrrolidin-1-yl)ethoxy]phenyl] ketone (Example 10) according to the procedure described in Example 7.

FDMS 663 (M+Li); Anal. for $C_{37}H_{39}LiN_2O_7S\cdot 2H_2O$: Calcd: C, 63.60; H, 6.20; N, 4.01; Found: C, 63.82; H, 6.03; N, 4.11.

EXAMPLE 12

Preparation of 2-[3-t-Butoxycarbonylmethoxy-4-[2-(1-pyrrolidinyl)ethoxy]phenyl]-3-[4-[2-(2-oxopyrrolidin-1-yl)ethoxy]-benzyl]benzo[b] thiophene Oxalate

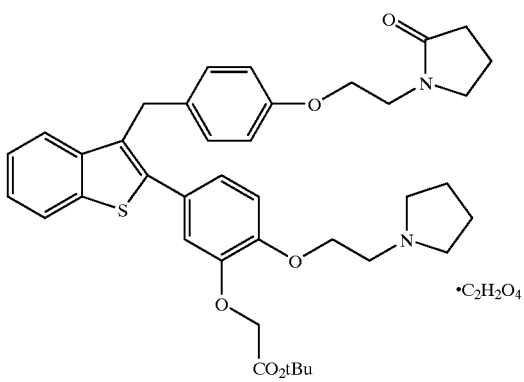

The title compound was prepared in 86% yield from 2-[3-hydroxy-4-[2-(1-pyrrolidinyl)ethoxy]phenyl]-3-[2-(2-oxopyrrolidin-1-yl)ethoxy]benzyl]benzo[b]thiophene (Example 6, Part F) and t-butyl bromoacetate by a procedure similar to that described in Example 6, Part G.

FDMS 671 (M+1); Anal. for $C_{39}H_{46}N_2O_6S\cdot 0.5 C_2H_2O_4$: Calcd: C, 67.11; H, 6.62; N, 3.91; Found: C, 66.77; H, 6.94; N, 3.80.

EXAMPLE 13

Preparation of 2-[3-Carboxymethoxy-4-[2-(1-pyrrolidinyl)-ethoxy]phenyl]-3-[4-[2-(2-oxopyrrolidin-1-yl)ethoxy]benzyl]-benzo[b] thiophene Trifluoroacetate

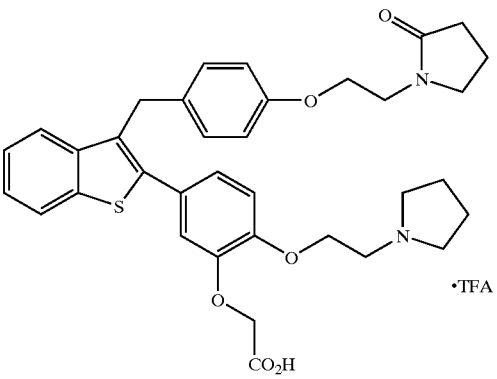

A solution of 2-[3-t-butoxycarbonylmethoxy-4-[2-(1-pyrrolidinyl)ethoxy]phenyl]-3-[4-[2-(2-oxopyrrolidin-1-yl)-ethoxy]benzyl]benzo[b]thiophene (Example 12; 250 mg, 0.374 mmol) in 2 mL of anisole was treated with 5 mL of TFA dropwise. After stirring for 2.5 days, the reaction mixture was poured into 15 mL of $H_2O$. The aqueous layer was extracted with EtOAc (2×25 mL) and concentrated in vacuo. The residue was dissolved in 2 mL of $H_2O$ and freeze-dried to afford 205 mg (0.281 mmol; 75%) of the title salt as a hygroscopic white solid.

FDMS 615 (M+1); Anal. for $C_{35}H_{38}N_2O_6S\cdot CF_3CO_2H\cdot 2.5H_2O$: Calcd: C, 57.43; H, 5.73; N, 3.62; Found: C, 57.03; H, 5.36; N, 3.84.

What is claimed is:

1. A compound of formula I (or a pharmaceutically acceptable salt thereof)

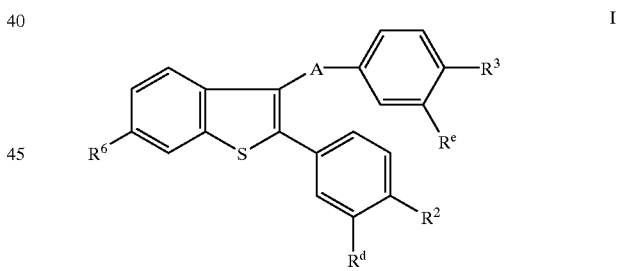

wherein

A is carbonyl or methylene;

$R^d$ is —[O—$(CH_2)_d$]$_c$—$R^c$ in which c is 0 or 1; d is 1, 2, or 3; and $R^c$ is carboxy, [(1–4C)alkoxy]carbonyl, hydroxymethyl or carbamoyl; provided that if c is 0, $R^c$ is carboxy, [(1–4C)alkoxy]carbonyl or carbamoyl; or Rd is —[O—$(CH_2)_d$]$_c$—$R^c$ in which c is 1; d is 1, 2, or 3; and $R^c$ is carboxy, [(1–4C)alkoxy]carbonyl, hydroxymethyl or carbamoyl;

$R^e$ is hydrogen, methyl, methoxy or halo;

$R^2$ is $R^{2a}$ or $R^{2b}$ in which $R^{2a}$ is —$X^2$—$(CH_2)_n$—$R^f$ in which $X^2$ is a direct bond, methylene or O; n is 1, 2 or 3; and $R^f$ is 5-tetrazolyl, carboxy, [(1–4C)alkoxy]carbonyl or hydroxymethyl;

$R^{2b}$ is —$X^2$—$(CH_2)_m$—$NR^aR^b$ in which $X^2$ is a direct bond, methylene or O; m is 1, 2 or 3; provided that when m is 1, then $X^2$ is a direct bond; and $R^a$ and $R^b$ are independently hydrogen or (1–3C)alkyl or the group $NR^aR^b$ is pyrrolidino, piperidino or morpholino;

$R^3$ is $R^{3a}$ or $R^{3b}$ in which $R^{3a}$ is 2-(2-oxopyrolidin-1-yl)ethoxy;

provided that $R^2$ is $R^{2b}$ when $R^3$ is $R^{3a}$;

$R^{3b}$ is —$X^3$—$(CH_2)_s$—$NR^sR^t$ in which $X^3$ is a direct bond, methylene or O; s is 1 or 2; provided that when s is 1, then $X^3$ is a direct bond; and $R^s$ and $R^t$ are independently hydrogen or (1–3C)alkyl or the group $NR^sR^t$ is pyrrolidino, piperidino or morpholino; and $R^6$ is hydrogen, hydroxy or methoxy.

2. The compound (or salt thereof) of claim 1 wherein (1–3C)alkyl is methyl, ethyl, propyl or isopropyl;

(1–4C)alkoxy is methoxy, ethoxy, propoxy, isopropoxy, butoxy or tert-butoxy; and halo is fluoro, chloro, bromo or iodo.

3. The compound (or salt thereof) of claim 1 wherein A is carbonyl or methylene;

$R^d$ is carboxy, methoxycarbonyl, carbamoyl, 3-(ethoxycarbonyl)propoxy, 3-carboxypropoxy, 4-amino-4-oxobutoxy, 4-hydroxybutoxy, (t-butoxycarbonyl)methoxy, or carboxymethoxy;

$R^e$ is hydrogen or methoxy;

$R^2$ is 2-(1-pyrrolidinyl)ethoxy, 3-carboxypropoxy, or 3-(methoxycarbonyl)propoxy;

$R^3$ is 2-(1-pyrrolidinyl)ethoxy, 1-pyrrolidinylmethyl or 2-(2-oxopyrrolidin-1-yl)ethoxy; and $R^6$ is hydrogen or hydroxy.

4. The compound (or salt thereof) of any one of claims 1–3 wherein $R^2$ is $R^{2a}$.

5. The compound (or salt thereof) of any one of claims 1–3 wherein $R^2$ is $R^{2b}$.

6. The compound (of salt thereof) of claim 1 or 3 wherein $R^3$ is $R^{3a}$.

7. The compound (or salt thereof) of claim 1 or 3 wherein $R^2$ is $R^{2b}$ and $R^3$ is $R^{3b}$.

8. The compound (or salt thereof) as claimed in any of claims 1–3 wherein $R^d$ is methoxycarbonyl, $R^e$ is hydrogen and $R^3$ is 2-(2-oxopyrrolidin-1-yl)ethoxy.

9. The compound of claim 1 which is 2-[3-methoxycarbonyl-4-[2-(1-pyrrolidinyl)ethoxy]phenyl]-3-[4-[2-(2-oxopyrrolidin-1-yl)ethoxy]benzyl]benzo[b]thiophene (or a pharmaceutically acceptable salt thereof).

10. A pharmaceutically acceptable salt of a compound of formula I as claimed in claim 1 which is an acid-addition salt made with an acid which provides a pharmaceutically acceptable anion or, for a compound which contains an acidic moiety, which is a salt made with a base which provides a pharmaceutically acceptable anion.

11. A pharmaceutical formulation comprising in association with a pharmaceutically acceptable carrier, diluent or excipient, a compound of formula I (or a pharmaceutically acceptable salt thereof) as provided in claim 1.

12. A process for preparing the compound of formula I, or a pharmaceutically acceptable salt thereof, as claimed in claim 1 which is selected from:

(A) for a compound of formula I in which $R^c$ is [(1–4C)alkoxy]carbonyl, oxidatively esterifying a corresponding compound of formula I in which $R^c$ is formyl using an oxidizing agent and the corresponding (1–4C)alkanol;

(B) for a compound of formula I in which $R^c$ is carbamoyl, oxidatively amidating a corresponding compound of formula I in which $R^c$ is formyl using an oxidizing agent and ammonia;

(C) for a compound of formula I in which $R^c$ is carboxy, oxidizing the formyl group of a corresponding compound of formula I in which $R^c$ is formyl;

(D) for a compound of formula I in which $R^c$ is [(1–4C)alkoxy]carbonyl, esterifying the carboxy group of a corresponding compound of formula I in which $R^c$ is carboxy;

(E) for a compound of formula I in which $R^d$ is —O—$(CH_2)_d$—$R^c$, alkylating the hydroxy group of a corresponding compound of formula I in which $R^d$ is hydroxy using an alkylating agent of formula X—$(CH_2)_d$—$R^c$ (or a protected derivative thereof) where X is a conventional leaving group;

(F) for a compound of formula I in which $R^c$ is carbamoyl, amidating the acid or an activated derivative thereof of a corresponding compound of formula I in which $R^c$ is carboxy;

(G) for a compound of formula I in which $R^c$ is hydroxymethyl, reducing the ester of a corresponding compound of formula I in which $R^c$ is [(1–4C)alkoxy]carbonyl;

whereafter, for any of the above procedures, when a functional group is protected using a protecting group, removing the protecting group;

whereafter, for any of the above procedures, when a pharmaceutically acceptable salt of a compound of formula I is required, it is obtained by reacting the basic form of such a compound of formula I with an acid affording a physiologically acceptable counterion, or, for ea compound of formula I which bears an acidic moiety, reacting the acidic form of such a compound of formula I with a base which affords a pharmaceutically acceptable cation, or by any other conventional procedure;

and wherein, unless otherwise described, A, $R^d$, $R^e$, $R^2$, $R^3$ and $R^6$ have the values described in claim 1.

13. A method of inhibiting thrombin in mammalian blood comprising administering to a mammal in need thereof an effective amount of a compound of formula I (or a pharmaceutically acceptable salt thereof) as described in claim 1.

14. The compound (of salt thereof) of claim 5 wherein $R^3$ is $r^{3a}$.

15. The compound (or salt thereof) of claim 5 wherein $R^2$ is $R^{2b}$ and $R^3$ is $R^{3b}$.

16. The compound (or salt thereof) as claimed in claim 5 wherein $R^d$ is methoxycarbonyl, $R^e$ is hydrogen and $R^3$ is 2-(2-oxopryrrolidin-1-yl) ethoxy.

* * * * *